United States Patent
Kim et al.

(10) Patent No.: US 11,898,169 B2
(45) Date of Patent: *Feb. 13, 2024

(54) SYNERGISTIC GENOME-NONINTEGRATING REPROGRAMMING BY MICRORNAS AND TRANSCRIPTION FACTORS

(71) Applicant: The McLean Hospital Corporation, Belmont, MA (US)

(72) Inventors: Kwang-Soo Kim, Lexington, MA (US); Young Cha, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 362 days.

This patent is subject to a terminal disclaimer.

(21) Appl. No.: 17/239,059

(22) Filed: Apr. 23, 2021

(65) Prior Publication Data

US 2021/0238556 A1    Aug. 5, 2021

Related U.S. Application Data

(63) Continuation of application No. 15/036,235, filed as application No. PCT/US2014/065371 on Nov. 13, 2014, now Pat. No. 11,001,809.

(60) Provisional application No. 61/904,934, filed on Nov. 15, 2013.

(51) Int. Cl.
*C12N 5/074* (2010.01)
*C12N 15/113* (2010.01)
*A61K 35/12* (2015.01)

(52) U.S. Cl.
CPC ............ *C12N 5/0696* (2013.01); *A61K 35/12* (2013.01); *C12N 15/113* (2013.01); *C12N 2310/141* (2013.01); *C12N 2501/602* (2013.01); *C12N 2501/603* (2013.01); *C12N 2501/604* (2013.01); *C12N 2501/606* (2013.01); *C12N 2501/65* (2013.01); *C12N 2506/1307* (2013.01); *C12N 2510/00* (2013.01); *C12N 2799/022* (2013.01)

(58) Field of Classification Search
CPC ................ C12N 5/0696; C12N 15/113; C12N 2310/141; C12N 2501/602; C12N 2501/603; C12N 2501/604; C12N 2501/606; C12N 2501/65; C12N 2506/1307; C12N 2510/00; C12N 2799/022; A61K 35/12

See application file for complete search history.

(56) References Cited

U.S. PATENT DOCUMENTS

2010/0075421 A1   3/2010   Yamanaka et al.
2011/0104125 A1   5/2011   Yu
2012/0100568 A1   4/2012   Pei et al.
2013/0065243 A1   3/2013   Mori et al.
2013/0102768 A1   4/2013   Yamanaka et al.

OTHER PUBLICATIONS

Oh et al. "Clinical applications of patient-specific induced pluripotent stem cells in cardiovascular medicine." Heart Mar. 2012;98(6):443-9. (Year: 2012).*
Aasen et al., "Efficient and rapid generation of induced pluripotent stem cells from human keratinocytes," Nature Biotechnology, Nov. 2008, 26(11):1276-1284.
Abujarour et al., "Induced pluripotent stem cells free of exogenous reprogramming factors," Genome Biol, 2009, 10(5):220.
Anokye-Danso et al, "Highly efficient miRNA-mediated reprogramming of mouse and human somatic cells to pluripotency," Cell Stem Cell, Apr. 2011, 8:376-388.
Anokye-Danso et al, "How microRNAs facilitate reprogramming to pluripotency," J. Cell Sci., Sep. 2012, 125(18):4179-4787.
Bellin et al, "Induced pluripotent stem cells: the new patient?," Nat. Rev. Mol. Cell Biol., Oct. 2012, 13(11):713-726.
Esteban et al., "Vitamin C Enhances the Generation of Mouse and Human Induced Pluripotent Stem Cells," Cell Stem Cell, Jan. 2010, 6(1):71-79.
Hu et al. "MicroRNA-302 increases reprogramming efficiency via repression of NR2F2," Stem Cells, 2013, 31(2):259-68.
Kim et al. "Technical note: Induction of pluripotent stem cell-like cells from chicken feather follicle cells," J Anim Sci., 2017, 95(8):3479-3486.
Kim et al., "Direct reprogramming of human neural stem cells by OCT4," Nature, Oct. 2009, 461:649-654.
Li et al., "Modeling abnormal early development with induced pluripotent stem cells from aneuploid syndromes," Human Molecular Genetics, Jan. 2012, 21(1):32-45.
Li et al., "Pluripotency can be rapidly and efficiently induced in human amniotic fluid-derived cells," Human Molecular Genetics, Aug. 2009, 18(22):4340-4349.
Liao et al., "MicroRNA Cluster 302-367 Enhances Somatic Cell Reprogramming by Accelerating a Mesenchymal-to-Epithelial Transition," J Biol Chem., 2011, 286(19): 17359-17364.
Liu et al., "Generation of Endoderm-Derived Human Induced Pluripotent Stem Cells from Primary Hepatocytes," Hepatology, May 2010, 51(5):1810-1819.
Loh et al., "Reprogramming of T Cells from Human Peripheral Blood," Cell Stem Cell, Jul. 2010, 7(1):15-19.

(Continued)

*Primary Examiner* — Titilayo Moloye
(74) *Attorney, Agent, or Firm* — Fish & Richardson P.C.

(57) ABSTRACT

Disclosed herein are methods of generating induced pluripotent stem cells. The method involves providing a quantity of somatic or non-embryonic cells, contacting the contacting the somatic or non-embryonic cells with a quantity of one or more programming factors and one or more RNA molecules, and culturing the somatic or non-embryonic cells for a period of time sufficient to generate at least one induced pluripotent stem cell. Various reprogramming factors and RNA molecules for use in the methods are disclosed herein. Also disclosed are cell lines and pharmaceutical compositions generated by use of the methods.

21 Claims, 15 Drawing Sheets

Specification includes a Sequence Listing.

(56) References Cited

OTHER PUBLICATIONS

Miyoshi et al, "Reprogramming of mouse and human cells to pluripotency using mature microRNAs," Cell, Jun. 2011, 8:633-638.

PCT International Preliminary Report on Patentability in International Appln. No. PCT/US2014/065371, dated May 26, 2016, 9 pages.

PCT International Search Report and Written Opinion in International Appln. No. PCT/US2014/065371, dated Mar. 11, 2015, 12 pages.

Poleganov et al., "Efficient Reprogramming of Human Fibroblasts and Blood-Derived Endothelial Progenitor Cells Using Nonmodified RNA for Reprogramming and Immune Evasion," Human Gene Therapy, Nov. 2015, 26(11):751-766.

Poriuncula et al., "MicroRNA signatures of iPSCs and endoderm-derived tissues," Gene Expr Patterns, 2013, 13(1-2):12-20.

Rossello et al., "Mammalian genes induce partially reprogrammed pluripotent stem cells in non-mammalian vertebrate and invertebrate species." eLife, 2013, 2:e00036.

Seki et al., "Generation of Induced Pluripotent Stem Cells from Human Terminally Differentiated Circulating T Cells," Cell Stem Cell, Jul. 2010, 7(1):11-14.

Stadtfeld et al., "Induced pluripotency: history, mechanisms, and applications," Genes Dev., 2010, 24(20):2239-6.

Staerk et al., "Reprogramming of Human Peripheral Blood Cells to Induced Pluripotent Stem Cells," Cell Stem Cell, Jul. 2010, 7(1):20-24.

Sugii et al., "Human and mouse adipose-derived cells support feeder-independent induction of pluripotent stem cells," Proceedings of the National Academy of Sciences, Feb. 2010, 107(8):3558-3563.

Sun et al., "Feeder-free derivation of induced pluripotent stem cells from adult human adipose stem cells," PNAS, Sep. 2009, 106(37):15720-15725.

Takahashi et al., "Induction of pluripotent stem cells from adult human fibroblasts by defined factors," Cell, Nov. 2007, 131:861-872.

Utikal et al., "Sox2 is dispensable for the reprogramming of melanocytes and melanoma cells into induced pluripotent stem cells," Journal of Cell Science, Oct. 2009, 122(19):3502-3510.

Wang et al., "Critical regulation of miR-200/ZEB2 pathway in Oct4/Sox2-induced mesenchymal-to-epithelial transition and induced pluripotent stem cell generation," Proc Natl Acad Sci USA, 2013, 110(8):2858-63.

Warren et al., "Highly efficient reprogramming to pluripotency and directed differentiation of human cells with synthetic modified mRNA," Cell Stem Cell, 2010, 7(5):618-30.

Yu et al, "Induced pluripotent stem cell lines derived from human somatic cells," Science, Nov. 2007, 318(5858):1917-1920.

Yu et al., "Efficient feeder-free episomal reprogramming with small molecules," PLoS One, 2011, 6(3):317557.

Zhou et al., "Generation of induced pluripotent stem cells using recombinant proteins," Cell Stem Cell, 2009, 4(5):381-4.

Zhou et al., "Generation of Induced Pluripotent Stem Cells from Urine," J. Am. Soc. Nephrol., Jul. 2011, 22(7):1221-1228.

* cited by examiner

| miRNA | MATURE SEQUENCE |
|---|---|
| miR-106a | C AAAGUG CUAACAGUGCAGGUAG |
| miR-106b | U AAAGUG CUGACAGUGCAGAU |
| miR-20b | C AAAGUG CUCAUAGUGCAGGUAG |
| miR-93 | C AAAGUG CUGUUCGUGCAGGUAG |
| miR-17 | C AAAGUG CUUACAGUGCAGGUAG |
| miR-291a | C AUCAAA GUGGAGGCCCUCUCU |
| miR-291b-5p | G AUCAAA GUGGAGGCCCUCUCC |
| miR-294 | A AAGUGC UUCCCUUUUGUGUGU |
| miR-295 | A AAGUGC UACUACUUUUGAGUCU |
| miR-302a | U AAGUGC UUCCAUGUUUUGGUGA |
| miR-302b | U AAGUGC UUCCAUGUUUUAGUAG |
| miR-302c | U AAGUGC UUCCAUGUUUCAGUGG |
| miR-302d | U AAGUGC UUCCAUGUUUGAGUGU |
| miR-25 | C AUUGCA CUUGUCUCGGUCUGA |
| miR-32 | U AUUGCA CAUUACUAAGUUGCA |
| miR-92a-1 | U AUUGCA CUUGUCCCGGCCUG |
| miR-92a-2 | U AUUGCA CUCGUCCCGGCCUCC |
| miR-92b | U AUUGCA CUCGUCCCGGCCUCC |
| miR-363 | A AUUGCA CGGUAUCCAUCUGUA |
| miR-367 | A AUUGCA CUUUAGCAAUGGUGA |
| miR-19a | U GUGCAA AUCUAUGCAAAACUGA |
| miR-19b | U GUGCAA AUCCAUGCAAAACUGA |
| miR-290-5p | A CUCAAA CUAUGGGGGCACUUU |
| miR-292 | A CUCAAA CUGGGGGCUCUUUUG |
| miR-200c | UAAUACUGCCGGGUAAUGAUGGA |
| miR-20a | UAAAGUGCUUAUAGUGCAGGUAG |
| miR-290-3p | AAAGUGCGCCUAGUUUUAAGCC |
| miR-18b | UAAGGUGCAUCUAGUGCUGUUAG |
| miR-291b-3p | AAAGUGCAUCCAUUUUGUUUGU |
| miR-293 | AGUGCCGCAGAGUUUGUAGUGU |
| miR-369-5p | AGAUCGACCGUGUUAUAUUCGC |

FIG. 1A

| DETERMINATION FOR RELATIVE REPROGRAMMING EFFICIENCY | |
|---|---|
| FACTOR COMBINATION | OBTAINED COLONY (EFFICIENCY) |
| Y3 | + (0.005±0.001%) |
| Y3+miR-17/92 | + (0.007±0.003%) |
| Y3+miR-106a/363 | + (0.009±0.001%) |
| Y3+miR-106b/25 | + (0.007±0.001%) |
| Y3+miR-200c | − |
| Y3+miR-371/373 | + (0.010±0.003%) |
| Y3+miR-302s | + (0.03±0.004%) |
| Y3+miR-302s+miR-17/92 | + (0.07±0.007%) |
| Y3+miR-302s+miR-106a/363 | + (0.09±0.006%) |
| Y3+miR-302s+miR-106b/25 | + (0.08±0.007%) |
| Y3+miR-302s+miR-200c | + (0.11±0.006%) |
| Y3+miR-302s+miR-371/373 | + (0.10±0.008%) |
| Y4 | + (0.15±0.008%) |
| Y4+miR-17/92 | + (0.18±0.006%) |
| Y4+miR-106a/363 | + (0.18±0.006%) |
| Y4+miR-106b/25 | + (0.17±0.008%) |
| Y4+miR-200c | − |
| Y4+miR-371/373 | + (0.16±0.008%) |
| Y4+miR-302s | + (0.26±0.012%) |
| Y4+miR-302s+miR-17/92 | + (0.17±0.008%) |
| Y4+miR-302s+miR-106a/363 | + (0.24±0.013%) |
| Y4+miR-302s+miR-106b/25 | + (0.24±0.006%) |
| Y4+miR-302s+miR-200c | + (0.39±0.012%) |
| Y4+miR-302s+miR-371/373 | + (0.18±0.006%) |

*FIG. 1C*

SYNERGISTIC GENOME-NONINTEGRATING REPROGRAMMING BY MICRORNAS AND TRANSCRIPTION FACTORS

RELATED APPLICATIONS

This Application is a continuation of U.S. patent application Ser. No. 15/036,235, filed May 12, 2016, which is a 35 U.S.C. § 371 National Phase Entry Application of International Application No. PCT/US2014/065371, filed Nov. 13, 2014, which designates the U.S. and which claims the benefit under 35 U.S.C. § 119(e) of U.S. Provisional Application Ser. No. 61/904,934, filed Nov. 15, 2013, the contents of each of which are incorporated herein by reference in their entirety.

GOVERNMENTAL SUPPORT

This invention was made with Government support under 1R01NS070577 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Apr. 22, 2021, is named Sequence Listing.txt and is 4947 kb in size.

FIELD OF THE INVENTION

The present invention relates to the field of regenerative medicine.

BACKGROUND

Induced pluripotent stem cells ("iPSCs") possess the hallmark stem cell properties of self-renewal (i.e., immortal) and differentiation capacity into cells derived from all three embryonic germ layers (i.e., pluripotency), and provide unprecedented potential for revolutionizing study and treatment of human disease. These cells can be obtained through "reprogramming", which involves dedifferentiation of cells from non-embryonic sources, such as adult somatic cells. The reprogramming process offers several advantages when compared to other types of pluripotent stem cells ("pSCs"), such as embryonic stem cells ("ESCs"). This includes the potential for deriving patient-specific cells that are immunologically compatible, and providing cell populations for drug screening, or models for investigating disease initiation and progression. In addition, derivation from non-embryonic sources obviates potential ethical concerns over embryonic source material.

Initial breakthroughs in the reprogramming of primate somatic cells into iPSCs were first reported by independently groups led by Thomson (Yu et al., Science 318:1917-1920 (2007) and Yamanaka (Takahashi et al., Cell 131:861-872 (2007)). Both groups delivered and expressed cDNA into human somatic cells through the use of viral vectors expressing factors related to pluripotency ("reprogramming factors"). Interestingly, initial reports differed in the combinations of transgenes successfully used for reprogramming. The Yamanaka group relied upon Oct-4, Sox-2, c-Myc (or 1-Myc) and Klf-4 (i.e., "Yamanaka factors"), while the Thomson group utilized Oct-4, Sox-2, Nanog, and Lin-28 (i.e., "Thomson factors"). Despite the difference in choice of reprogramming factors, their delivery into, and expression by, somatic cells allowed acquisition of pSC-specific characteristics. This includes cells with characteristic stem cell colony morphology (e.g., round bright clusters, high cytoplasm to nucleus ratio), proliferation capacity and pluripotency, as well as proper gene and surface marker expression.

These initial reports were followed by attempts to obviate concerns over the use of integrative viral delivery systems by the Yamanaka and Thomson groups, given the intended clinical aspirations for iPSCs. Latent viral proteins possess potential disease-causing effects by for example, integration resulting in chromosomal mutations/disruptions. Despite these many efforts to optimize reprogramming techniques, they have nevertheless been plagued by poor efficiency (often far less than 0.1%), irreproducibility, and limited extensibility across different target host cell types. Further, the great majority of iPSCs used for disease mechanism studies (~96%) are still generated by retroviral/lentiviral reprogramming methods. Bellin et al., Nat Rev Mol Cell Biol 13:713-726 (2012). While certain non-integrating reprogramming methods (e.g., Adenovirus, Sendai virus, episomal, mRNA, mature microRNA, and direct protein methods) do exist, these methods are so much less efficient than retro/lentiviral methods that their widespread application has been severely hampered.

Given the eventual therapeutic goal of generating patient-specific, immunocompatible biological material, there is a great need in the art to establish a robust and reproducible means for reprogramming cells that avoids use of viral components, while providing effective reprogramming in significant quantities. Such improved methods would ideally possess high efficiency of reprogramming, consistent reproducibility, and be readily extendible to a variety of cell types.

Described herein are compositions, methods and kits for reprogramming somatic cells to induced pluripotent stem cells and/or the other cell types, including methods that do not rely on chromosomal integration. Specifically, reprogramming transcription factors that regulate cell fate, in combination with microRNAs can be applied for successful reprogramming, and without use of viral vectors. Combinations of reprogramming factors such as the Yamanaka Factors (e.g., Oct-4, Sox-2, Klf-4 and 1-Myc) and various microRNAs (e.g., as miR-302, -200, and -367) provided a marked synergistic effect when delivered in lentiviral vectors. This powerful synergistic effect facilitates faster and more efficient reprogramming of human fibroblasts into iPSCs, as the combination of both reprogramming transcription factors and microRNAs are described herein as providing significant improvements in reprogramming efficiency. Importantly, these results can be extended to other non-integrative methods such as episomal vectors or Adenoviral systems, as well as mature RNAs and microRNAs. These results establish non-integrative methods as feasible alternatives by removing barriers related to inefficiency that previously hampered their adoption. Together, the described invention leads to fast and efficient generation of iPSCs and differentiated cells without genome disruptions, providing a renewable resource of undifferentiated and differentiated cells for disease modeling, drug screening, and/or regenerative medicine applications.

SUMMARY OF THE APPLICATION

One aspect of the invention relates to a method of generating induced pluripotent stem cells, comprising, providing a quantity of somatic or non-embryonic cells, contacting the somatic or non-embryonic cells with a quantity of one or more reprogramming factors and one or more RNA molecules, culturing the somatic or non-embryonic cells for a period of time sufficient to generate at least one induced pluripotent stem cell.

In one embodiment of the herein disclosed methods, contacting the cells with a quantity of the one or more reprogramming factors and one or more RNA molecules comprises transduction, nucleofection, electroporation, direct injection and/or transfection.

In one embodiment of the herein disclosed methods, the one or more reprogramming factors comprise one or more factors selected from the group consisting of: Oct-4, Sox-2, Klf-4, c-Myc, Lin-28, SV40 Large T Antigen ("SV40LT"), and short hairpin RNAs targeting p53 ("shRNA-p53").

In one embodiment of the herein disclosed methods, the one or more reprogramming factors are Oct-4, Sox-2, Klf-4, and c-Myc.

In one embodiment of the herein disclosed methods, the one or more RNA molecules are microRNAs.

In one embodiment of the herein disclosed methods, the microRNAs comprise miR-106a, miR-106b, miR-106b25, miR-20b, miR-93, miR-17, miR-291a, miR-291b-5p, miR-294, miR-295, miR-302a, miR-302b, miR-302c, miR-302d, miR-25, miR-32, miR92a-1, miR92a-2, miR92b, miR-363, miR-367, miR-19a, miR-19b, miR-290-5p, miR-292, miR-200c, miR-20a, miR-290-3p, miR-18b, miR-291b-3p, miR-293, and/or miR-369-5p, derivatives and orthologs thereof.

In one embodiment of the herein disclosed methods, the microRNAs comprise at least one miR-302 cluster member, at least one miR-367 cluster member, and at least one miR-200 cluster member.

In one embodiment of the herein disclosed methods, the one or more microRNAs are miR-106a, miR-106b-25 miR-302a, miR-302b, miR-302c, miR-302d, miR-363, miR-367, and miR-200c.

In one embodiment of the herein disclosed methods, the one or more reprogramming factors are Oct-4, Sox-2, Klf-4, and c-Myc and the one or more RNA molecules are miR-106a, miR-106b-25 miR-302a, miR-302b, miR-302c, miR-302d, miR-363, miR-367, and miR-200c microRNAs.

In one embodiment of the herein disclosed methods, the one or more reprogramming factors and one or more RNA molecules are encoded in one or more viruses.

In one embodiment of the herein disclosed methods, the one or more viruses are non-integrative viruses.

In one embodiment of the herein disclosed methods, the non-integrative virus is an Adenovirus or Sendai virus.

In one embodiment of the herein disclosed methods, the one or more reprogramming factors and one or more RNA molecules are encoded in one or more non-integrative vectors.

In one embodiment of the herein disclosed methods, the non-integrative vector is an episomal or minicircle vector.

In one embodiment of the herein disclosed methods, the reprogramming media comprises at least one chemical induction molecule.

In one embodiment of the herein disclosed methods, wherein the reprogramming media comprises culturing the somatic or non-embryonic cells in a reprogramming media for at least 7 days.

In one embodiment of the herein disclosed methods, culturing the somatic or non-embryonic cells in a reprogramming media is for at least 7, 8, 9, 10, 11, 12, 13, 14, 15, or 16 days.

In one embodiment of the herein disclosed methods, culturing the somatic or non-embryonic cells in a reprogramming media is for 8 to 14 days.

In one embodiment of the herein disclosed methods, generating induced pluripotent stem cells comprises further culturing the somatic or non-embryonic cells in an induction media for at least 10 days.

In one embodiment of the herein disclosed methods, culturing the somatic or non-embryonic cells in an induction media is for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

In one embodiment of the herein disclosed methods, further culturing the somatic or non-embryonic cells in an induction media is for 1 to 12 days.

In one embodiment of the herein disclosed methods, the induction media is a serum-free media.

In one embodiment of the herein disclosed methods, the method further comprises isolating at least one induced pluripotent stem cell.

Another aspect of the invention relates to a cell line comprising induced pluripotent stem cells generated by the method of any of the herein described methods. In one embodiment, the cell line comprises cells substantially free of exogenous DNA.

Another aspect of the invention relates to a pharmaceutical composition comprising a quantity induced pluripotent stem cells generated by the any of the herein disclosed methods, and a pharmaceutically acceptable carrier.

Another aspect of the invention relates to an induced pluripotent stem cell line substantially free of exogenous DNA.

BRIEF DESCRIPTION OF DRAWINGS

FIG. 1A-FIG. 1C shows experimental results that indicate microRNAs enriched in Pluripotent Stem Cells. (A) As shown in this figure, various microRNAs are expressed and enriched in pluripotent stem cells. Both the sequence of microRNAs, their seed sequence in various colors, and cluster organization are shown (from Anokye-Danso et al., *J Cell Sci.* 125: 4179-4787 (2012)). These sequences correspond to SEQ ID NO: 1-SEQ ID NO: 31, respectively, in order of appearance. (B) and (C) Identification of microRNAs that enhance the generation of iPSC-like colonies. Human fibroblasts (Nuff) were transduced with lentiviral vectors expressing the Yamanaka factors Oct-4, Sox-2, c-Myc and Klf-4 ("Y4") and each of potential microRNAs. The number of iPSC-like colonies (alkaline phosphatase-positive) were counted at day 14 as a measurement of reprogramming efficiency.

DETAILED DESCRIPTION

Figure 1B:
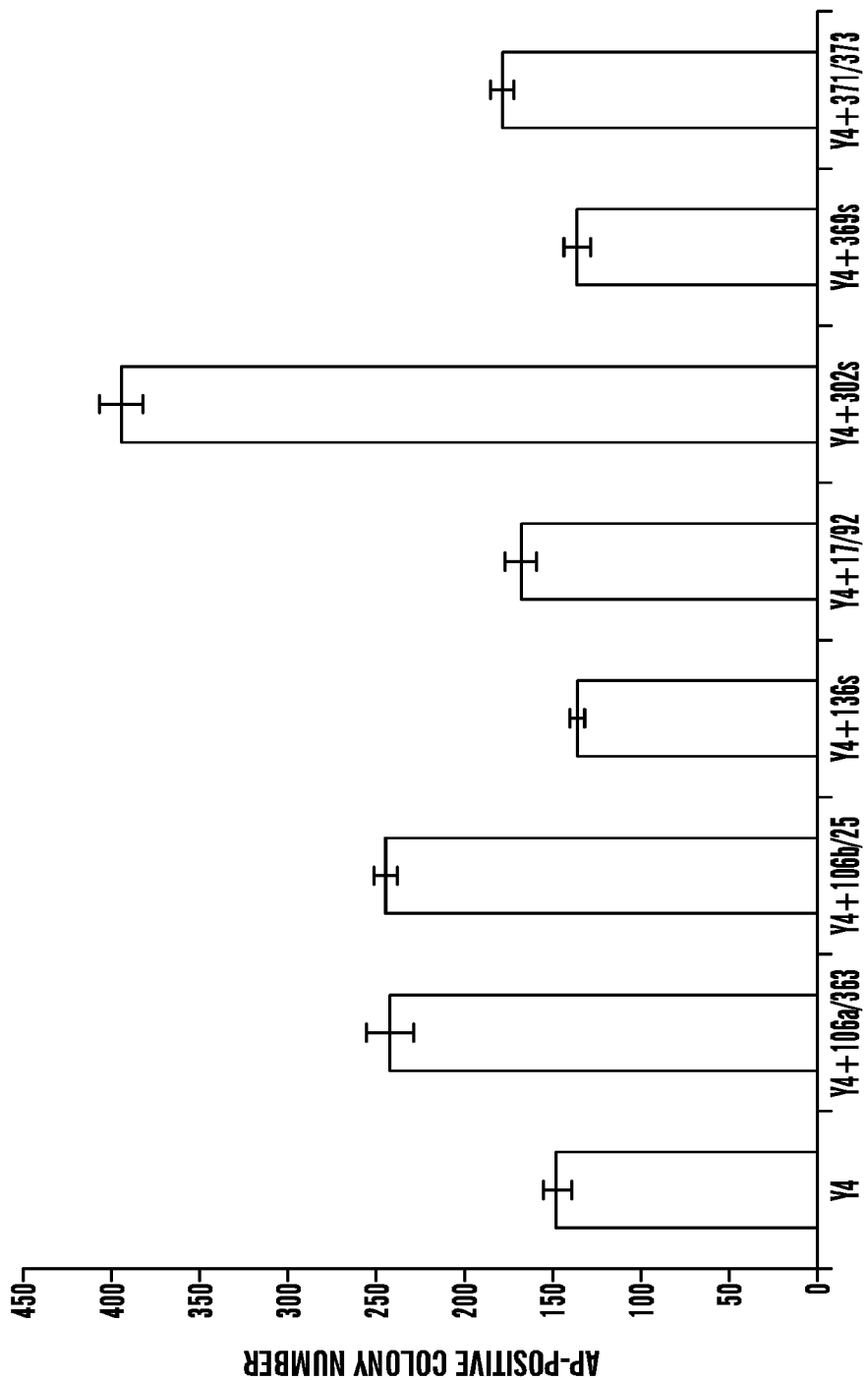

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 4$^{th}$ ed., J. Wiley & Sons (New York, N.Y. 2012); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 4th ed., Cold Spring Harbor Laboratory Press (Cold Spring Harbor, N.Y. 2012); provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As described, integrative viral delivery is the present leading choice for "efficient" reprogramming of somatic cells into induced pluripotent stem cells ("iPSCs"), although described "efficiency" in this context may mean less than 0.1% are successfully reprogrammed. For non-integrative reprogramming, several categories have emerged as possible alternatives: 1) integration-defective virus, 2) episomal vectors 3) direct RNA/microRNA delivery, 4) direct protein delivery and 5) chemical induction. However, a significant obstacle for adoption of these methods is that they are widely understood to be even less efficient than retro/lentiviral methods, thereby hampering their widespread application. If notable improvements can be established for non-integrative approaches, techniques such as integration-defective virus and episomal vectors allows for generation of iPSCs substantially free of the vector components used in their production. These non-integrative techniques would thus limit risk of introducing chromosomal mutations/disruptions, allowing realization of clinical applications for iPSCs and cells derived therefrom.

As described, the Inventors have discovered that reprogramming transcription factors, in combination with microRNAs can be successfully applied in reprogramming methods to provide a powerful synergistic effect enhancing the reprogramming efficiency. Although addition of specific microRNAs has been reported to enhance the efficiency of reprogramming, the context of such studies is extremely limited. For example, the few existing studies on the role of microRNAs in reprogramming has been done with only a limited number of reprogramming transcription factors. Thus, it is entirely unknown how a full slate of reprogramming transcript factors (e.g., all four Yamanaka factors Oct-4, Sox-2, c-Myc and Klf-4) operate in combination with microRNAs, and what roles these reprogramming factors play in dedifferentiation of somatic cells. It is further unknown whether iPSCs can be generated using only microRNAs. Certain reports, such as Anokyc-Danso et al. claim that lentiviral expression of miR-302/367 clusters can reprogram mouse and human fibroblasts with 100-times greater efficiency than those four transcription factors-based method. Anokye-Danso et al., *Cell Stem Cell* 8: 376-388 (2011). Similarly, Miyoshi et al. claim that transfection of mature microRNAs miR-200c, miR-302s, and miR-369s can generate human iPSCs. Miyoshi et al., *Cell* 8:633-638 (2011). However, it is not clearly if these results are readily reproducible.

microRNAs, generally. microRNAs are small non-coding RNAs with an average length of 22 nucleotides. These molecules act by binding to complementary sequences within mRNA molecules, usually in the 3' untranslated (3'UTR) region, thereby promoting target mRNA degradation or inhibited mRNA translation. The interaction between microRNA and mRNAs is mediated by what is known as the "seed sequence", a 6-8-nucleotide region of the microRNA that directs sequence-specific binding to the mRNA through imperfect Watson-Crick base pairing. More than 900 microRNAs are known to be expressed in mammals. Many of these can be grouped into families on the basis of their seed sequence, thereby identifying a "cluster" of similar microRNAs. An example of various microRNAs known to be expressed in pSCs is shown in FIG. 1.

The potentially vital role of microRNAs in reprogramming and establishment of the pluripotent has been reported, but specific mechanisms remain largely unknown. Initial discoveries studying mouse ESCs identified three microRNAs (mir-200c, mir-302s, and mir-369s), that were overexpressed in mouse ES cells relative to mouse adipose stromal cells. These microRNAs targeted processes that, in the mouse, enhanced reprogramming. Early reports suggested mir-200c inhibited epithelial-mesenchymal transitions ("EMT"), mir-302s was part of a regulatory circuit with Oct-4 that maintained pluripotency, and mir-369s inhibited Zeb-2-related TGFβ signaling. Importantly, when compared to methods relying on reprogramming transcription factors, which can take 30-45 days to complete reprogramming, mature forms of these three microRNAs in human dermal fibroblasts and adipose stromal cells, allowed successful reprogramming and formation of iPSC-like colonies in as little as 20 days after the first transfection. Characterization of these colonies confirmed that they had markers of pSCs with the capacity to form cells from each of the three germ layers in mouse teratoma assays. However, beyond this neat organization of microRNAs, subsequent results have demonstrated considerable overlap and/or regulatory interaction between these different mechanisms and exploiting microRNAs for reprogramming applications must clearly anticipate their specific roles and interactions.

miR-290/372 cluster. The miR-290/372 cluster contains multiple mature microRNAss with seed sequences similar or identical to miR-302 or the miR-17 cluster, and is the most abundantly expressed population in pSCs, comprising the majority (up to 70%) of microRNAs in undifferentiated ESCs. Of note, the miR-290 cluster is not expressed in human cells, but human miR-372 is orthologous to the mouse miR-294, and promotes reprogramming of human fibroblasts.

Several members of the miR-290 cluster, namely miR-291 to 3p, miR-294 and miR-295, as well as members of the miR-302 cluster, appear to belong to the ESC-specific cell cycle-regulating ("ESCC") group of microRNAs, which direct repression of key pSC cell cycle regulators. Specifically, ESC-cell cycle regulating microRNAs target multiple inhibitors of the CyclinE-Cdk2 pathway, thereby ensuring a rapid G1-S transition. Beside their function in maintaining pluripotency, microRNAs may also possess a separate function for subsequent control of pSC differentiation, as these miRs are specifically upregulated in ESCs after induction of differentiation to reduce the expression of pluripotency factors, a prerequisite to acquire a differentiated phenotype. For example, miR-296 appears to repress pluripotency factor, Nanog, whereas miR-134 and miR-470 appear to target the pluripotency factors Nanog, Oct4, and Sox2.

Based on high expression of miR-290 family in pSCs, initial attempts overexpressing members of this family in combination with Oct-4, Sox-2, and Klf-4 in mouse embryonic fibroblasts. MiR-291-3p, miR-294, and miR-295 were reported to increase the efficiency of reprogramming, whereas the other members of the miR-290 cluster, miR-292 to 3p and miR-293, were not effective. The most significant effects were achieved by overexpressing miR-294, which increased the efficiency to 75% of that achieved with the three reprogramming factors alone. The miR-294 microRNA additionally increased the kinetics of reprogramming, but was not sufficient to reprogram fibroblasts in the absence of additional reprogramming factors. These results suggest that certain microRNA functions may not operate effectively in isolation, requiring the presence of other reprogramming transcription factors or microRNAs for dedifferentiation to initiate and take hold in the target somatic cell.

miR-302 cluster. As described, members of the miR-290/372 cluster can share the same seed sequence as the miR-302 family. Together, application of these microRNA members were capable enhancing reprogramming efficiency of mouse fibroblast and the overexpression of the human miR-302 cluster in combination with miR-372 (the orthologs to the mouse miR-290 cluster members), and the reprogramming factors Oct-4, Sox-2, Klf-4, and c-Myc promoted the induction of pluripotency of human fibroblasts. In humans, the miR-302/367 ESCC microRNAs cluster is also a direct Oct-4/Sox-2 target that inhibits the cell cycle regulator cyclin D1. Altogether, this cluster contains five microRNAs, with the same seed sequence, AAGUGCU. Without being bound by any particular theory, it is appears that miR-302 functions as a gene silencer and simultaneously downregulates multiple key epigenetic regulators. In particular, targets of miR-302 cluster appear to include at least four epigenetic regulators, including Aof-1, Aof-2, Mecp1-p66, and Mecp2. Silencing of these epigenetic regulators induces global DNA demethylation, a key initiation step in altering somatic gene expression patterns in cells, thereby defining the cells' properties. Once this alteration begins, global demethylation resets the differentiated gene expression patterns to a highly uniform pSC-like profile. The resulting transcription machinery is activated for expression of pSC-specific genes and required for iPSC formation.

More specifically, Aof-1 and Aof-2 suppress gene expression through the demethylation of histone 3 on lysine 4 (H3K4). Since downregulation of Aof-2 correlates with decreased Dnmt-1 expression levels, miR-302 cluster also has an indirect effect on DNA methylation. Moreover, Mecp1-p66 and Mecp2 are believed to be important epigenetic regulators that bind to specific methylated regions of DNA, and confirmed that miR-302b target Mecp2. Another recent report indicated that, in human ESCs, miR-302 cluster promotes bone morphogenetic protein ("BMP") signaling through the repression of its inhibitors, Tob-2, Dazap-2, and Slain-1. miR-302 cluster also targets many cell cycle proteins, including the G1-S transition cell cycle regulators Cyclin D1 and Cdk-2. The ectopic expression of miR-302a causes the translational inhibition of Cyclin D1 and thus results in an accumulated population of primary and malignant cells in the S phase and a decreased population of cells in the G1 phase, which resembles the cell cycle profile of ESC.

It has been reported that the miR-302 cluster is capable inducing pluripotency in the absence of additional reprogramming factors in cancer cells, through application of miR-302 cluster member overexpression, along with and miR-367, allegedly resulting in directly reprogrammed mouse and human somatic cells. This is allegedly without additional reprogramming transcripts factors. However, it is not clearly if these results are readily reproducible. As described, certain microRNA functions may not operate effectively in isolation, requiring the presence of other reprogramming transcription factors or microRNAs for dedifferentiation to initiate and take hold in the target somatic cell.

miR-34 cluster. As the above described studies of microRNAs in pluripotent maintenance and fate specification have focused largely on their interactions with pluripotent transcription factors, cell cycle regulators and epigenetic regulators, another key actor in reprogramming has emerged as a potential barrier for somatic reprogramming: p53. Although a classic tumor suppressor gene, p53 is also known to regulate cell proliferation, survival and genomic stability in pSCs. Endogenous functional roles of basal p53 expression in ES cells were first suggested by results demonstrating increase hyperproliferation, apoptosis resistance and compromised genomic stability in p53-deficient human ES cells, leading some attempts to rely on short hairpin targeting of p53 ("shRNA-p53") as an additive in reprogramming studies.

However, it is clear that endogenous microRNAs interact with p53, and this mechanism can possibly be exploited to obviate the reprogramming barriers presented by p53 and its related pathways. The first microRNAs identified as direct p53 targets were the miR-34 family microRNAs, including miR-34a, miR-34b and miR-34c, all in two separate genomic loci. The functional readout of miR-34 microRNAs, at least in overexpression studies, depends on cell type and biological contexts and comprises a broad range of biological processes downstream of p53, including cell cycle, cellular senescence, apoptosis, stem cell differentiation and mesodermal development. p53 induces miR-34 microRNAs during reprogramming, and miR-34 deficiency partially recapitulates the increase in reprogramming efficiency caused by p53 deficiency. Unlike p53 loss, which enhances reprogramming at the expense of iPS cell pluripotency, genetic ablation of mir-34a is believed to promote pluripotent cell generation, without compromising self-renewal or differentiation. The miR-34 microRNAs, particularly miR-34a, cooperate with p21 to mediate suppression of somatic reprogramming by p53. Although enforced miR-34a expression leads to cell cycle arrest, senescence and apoptosis in a cell type- and context-dependent manner, miR-34a deficiency in mouse embryonic fibroblasts ("MEFs") does not have a significant proliferative advantage or apoptotic protection during somatic reprogramming. These surprising findings suggest that miR-34a suppresses somatic reprogramming, largely through a mechanism independent of cell cycle control or apoptosis.

miR-200 cluster: While it is well-known that miR-200 cluster in general plays a role in tumor progression, reported roles in the reprogramming process is considerably murkier. The miR-200 family of microRNAs, including miR-200a, miR-200b, miR-200c, miR-141 and miR-429, were initially characterized as inhibitors of EMT that functioned by repressing Zeb-1, Zeb-2 and Bmi-1. For example, miR-200 cluster members repress EMT through direct down-regulation of Zeb-1 and Zeb-2, transcriptional repressors of E-cadherin, a known epithelial cell marker. Furthermore, miR-200c mimic strongly induces Cdh1, Epcam, and Ocln expression and suppresses the expression level of Snail and Slug. Despite the importance of EMT in development, physiology and tumor invasion, EMT and its reverse process, MET (mesenchymal-to-epithelial transition), were characterized only recently in differentiation and somatic reprogramming. MET is the initial step of MEF reprogramming upon introduction of reprogramming factors, which correlates with induction of miR-200 microRNAs in a BMP-dependent manner. Consistently, enforced miR-200 expression enhances MET and facilitates MEF reprogramming.

Notably, miR-200c is a validated p53 transcriptional target and p53 appears to regulate EMT and stem cell properties through modulation of miR-200c. All these reports suggest that the miR-200 cluster may have an integral role in modulating EMT and stem cell phenotype as regulated by p53. Although it is reported that miR-200 microRNAs promote reprogramming so potently that miR-200c, miR-302 and miR-367 microRNAs alone are sufficient to generate iPS cells in the absence of any protein coding reprogramming factors, these findings are at odds with the suppressive role of p53 during iPSC cell generation as well as miR-200c-mediated repression of sternness by p53 in breast cancer cells and in further view of the ability of p53 to induce miR-200c in multiple cell types. These observations raise several questions about the role of the p53-miR-200c axis in iPS cell generation.

Despite the efforts in studying microRNAs and stem cell properties, regulation of the plasticity of microRNAs-sternness is not clear and the molecular mechanisms of miR-200 cluster that regulate the reprogramming procedure is also largely unknown. Thus, a key aspect of the Inventors' work is discovering the functional role of miR-200 cluster (especially, miR-200c) in somatic cell reprogramming. As it is well-known that p53 pathway suppresses iPSC generation, and transactivation of miR-200c is one of the diverse functions of p53, the Inventors investigated whether miR-200c inhibits the survival of partially reprogrammed cells through regulating downstream target genes which is involved in p53 pathway.

Other microRNA clusters. In addition to the aforementioned clusters, a wide variety of other microRNA clusters are known to play a role in stem cell identity. For example, it has been reported that overexpression of the microRNA clusters miR-106a/363 and miR-302/367 leads to increased efficiency of iPS cell generation by accelerating MET. Recently, three miR clusters, namely the miR-17/92 cluster, the miR-106b/25 cluster, and the miR-106a/363 cluster, which share the same or very similar seed sequences with the miR-302 cluster members, were shown to be highly induced during reprogramming and overexpression of the miR-106b-25 cluster members miR-93 and miR-106b enhanced iPS cell induction in the presence of three (Oct-4, Sox-2, and Klf-4) or four (Oct-4, Sox-2, Klf-4, and c-Myc (or 1-Myc)) reprogramming factors The capacity of the miR-290, miR-302, miR-17, and miR-25 cluster members to enhance reprogramming in the presence of the pluripotency factors was confirmed in a recent unbiased screen of 379 microRNAs. In that screen, the authors additionally identified the microRNAs family miR-130/301/721 to augment reprogramming of fibroblasts with Oct-4, Sox-2, and Klf-4.

Non-integrative Vectors. Ultimately a keen understanding of mechanisms for microRNA in reprogramming processes will allow generation of induced pluripotent stem cells substantially free of exogenous DNA, thereby limiting risk of chromosomal mutations/disruptions.

One example of a non-integrative includes the Epstein Barr oriP/Nuclear Antigen-1 ("EBNA1") vector, which is capable of limited self-replication and known to function in mammalian cells. As containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free iPSCs.

More specifically, persistent expression of reprogramming factor encoded in an oriP/EBNA1 vector occurs across multiple cell divisional cycles. Sufficiently high levels of reprogramming factors across several cell divisions allows for successful reprogramming even after only one infection. While sustained expression of reprogramming factors is understood to be beneficial during initial programming stages, otherwise unlimited constitutive expression would hamper subsequent stages of the reprogramming process. For example, unabated expression of reprogramming factors would interfere with subsequent growth, development, and fate specification of the host cells.

In another example of non-integrative vectors, minicircle vectors are circularized vectors in which the plasmid backbone has been released leaving only the eukaryotic promoter and cDNA(s) that are to be expressed. Such minicircle vectors have been used with reprogramming transcription factors Oct-4 Sox-2, nanog, and Lin-28 for reprogramming human adipose stem cells, although the reported protocol required three transfections of the minicircle vector: initial electroporation, followed by two lipid-based transfections, and even then only resulting in a reprogramming efficiency of 0.005%.

Non-integrative Virus. Similarly, non-integrative adenoviruses eliminate the risks posed by integrative retroviruses, as they do not incorporate their genome into the host DNA. Although iPSCs have been generated by adenoviral methods, they have extremely low reprogramming efficiency. For example, first attempts to create human iPSCs with adenoviral delivery of the four Yamanaka factors resulted in a reprogramming efficiency of only 0.0002% in human fetal fibroblasts.

Another non-integrative virus is RNA Sendai virus, which can produce protein without entering the nucleus of an infected cell. The F-deficient Sendai virus vector remains in the cytoplasm of infected cells for a few passages, but is diluted out quickly and completely lost after several passages (e.g., 10 passages). Similar to other non-integrative systems described herein, efficiency is low, although reported efficiencies of up to 0.1% have been described, which is comparable retro- or lentivirus-based techniques.

Reprogramming Factors. In addition to these choices in vector designs, the specific combinations of reprogramming factors implemented in the literature have varied. As mentioned, reprogramming factors that have been used include pluripotency-related genes Oct-4, Sox-2, Lin-28, Nanog, Sa114, Fbx-15 and Utf-1. These factors, traditionally are understood be normally expressed early during development and are involved in the maintenance of the pluripotent potential of a subset of cells that will constituting the inner cell mass of the pre-implantation embryo and post-implantation embryo proper. Their ectopic expression of is believed to allow the establishment of an embryonic-like transcriptional cascade that initiates and propagates an otherwise dormant endogenous core pluripotency program within a host cell.

Certain other reprogramming determinants, such as Tert, Klf-4, c-Myc, SV40 Large T Antigen ("SV40LT") and short hairpin RNAs targeting p53 ("shRNA-p53") have been applied. There determinants may not be potency-determining factors in and of themselves, but have been reported to provide advantages in reprogramming. For example, Tert and SV40LT are understood to enhance cell proliferation to promote survival during reprogramming, while others such as short hairpin targeting of p53 inhibit or eliminate reprogramming barriers, such as senescence and apoptosis mechanisms. In each case, an increase in both the speed and efficiency of reprogramming is observed.

While various vectors and reprogramming factors in the art appear to present multiple ingredients capable of establishing reprogramming in cells, a high degree of complexity occurs when taking into account the stoichiometric expression levels necessary for successful reprogramming to take hold. For example, somatic cell reprogramming efficiency is reportedly fourfold higher when Oct-4 and Sox-2 are encoded in a single transcript on a single vector in a 1:1 ratio, in contrast to delivering the two factors on separate vectors. The latter case results in a less controlled uptake ratio of the two factors, providing a negative impact on reprogramming efficiency. One approach towards addressing these obstacles is the use of polycistronic vectors, such as inclusion of an internal ribosome entry site ("IRES"), provided upstream of transgene(s) that is distal from the transcriptional promoter. This organization allows one or more transgenes to be provided in a single reprogramming vector, and various inducible or constitutive promoters can be combined together as an expression cassette to impart a more granular level of transcriptional control for the plurality of transgenes. These more specific levels of control can benefit the reprogramming process considerably, and separate expression cassettes on a vector can be designed accordingly as under the control of separate promoters.

Although there are advantages to providing such factors via a single, or small number of vectors, upper size limitations on eventual vector size do exist, which can stymie attempts to promote their delivery in a host target cell. For example, early reports on the use of polycistronic vectors were notable for extremely poor efficiency of reprogramming, sometimes occurring in less than 1% of cells, more typically less than 0.1%. These obstacles are due, in-part, to certain target host cells possessing poor tolerance for large constructs (e.g., fibroblasts), or inefficient processing of IRES sites by the host cells. Moreover, positioning of a factor in a vector expression cassette affects both its stoichiometric and temporal expression, providing an additional variable impacting reprogramming efficiency. Thus, some improved techniques can rely on multiple vectors each encoding one or more reprogramming factors in various expression cassettes. Under these designs, alteration of the amount of a particular vector for delivery provides a coarse, but relatively straightforward route for adjusting expression levels in a target cell.

Finally, in some instances, there may be further benefits in altering the chemical and/or atmospheric conditions under which reprogramming will take place. For example, as the pre-implantation embryo is not vascularized and hypoxic (similar to bone marrow stem-cell niches) reprogramming under hypoxic conditions of 5% $O_2$, instead of the atmospheric 21% 02, may further provide an opportunity to increase the reprogramming efficiency. Similarly, chemical induction techniques have been used in combination with reprogramming, particularly histone deacetylase (HDAC) inhibitor molecule, valproic acid (VPA), which has been found wide use in different reprogramming studies. At the same time, other small molecules such as MAPK kinase (MEK)-ERK ("MEK") inhibitor PD0325901, transforming growth factor beta ("TGF-β") type I receptor ALK4, ALK5 and ALK7 inhibitor SB431542 and the glycogen synthase kinase-3 ("GSK3") inhibitor CHIR99021 have been applied for activation of differentiation-inducing pathways (e.g. BMP signaling), coupled with the modulation of other pathways (e g inhibition of the MAPK kinase (MEK)-ERK pathway) in order to sustain self-renewal. Other small molecules, such as Rho-associated coiled-coil-containing protein kinase ("ROCK") inhibitors, such as Y-27632 and thiazovivin ("Tzv") have been applied in order to promote survival and reduce vulnerability of pSCs to cell death, particularly upon single-cell dissociation.

Target Cells. In addition to the choice of delivery vectors, reprogramming factor combinations, and conditions for reprogramming, further variations must consider the nature of the host target cell for reprogramming. To date, a wide variety of cells have served as sources for reprogramming including fibroblasts, stomach and liver cell cultures, human keratinocytes, adipose cells, and frozen human monocyte. Clearly, there is a wide and robust potential for dedifferentiation across many tissues sources. Nevertheless, it is widely understood that depending on the donor cell type, reprogramming is achieved with different efficiencies and kinetics. For example, although fibroblasts remain the most popular donor cell type for reprogramming studies, other types of cells such as human primary keratinocytes transduced with Oct-4, Sox-2, Klf-4 and c-Myc have been reported to reprogram 100 times more efficiently and twofold faster. Additionally, some other cell types, such as cord blood cells, may only require a subset of reprogramming factors, such as Oct-4 and Sox-2 for dedifferentiation to take hold, while neural progenitor cells may only require Oct-4. Without being bound to any particular theory, it is believed that differences in reprogramming efficiency and/or reprogramming factor requirements of specific host cells result from high endogenous levels of certain reprogramming factors and/or intrinsic epigenetic states that are more amenable to reprogramming.

Characterization of pSCs. Following successful reprogramming, clonal selection allows for generation of pluripotent stem cell lines. Ideally, such cells possess requisite morphology (i.e., compact colony, high nucleus to cytoplasm ratio and prominent nucleolus), self-renewal capacity for unlimited propagation in culture (i.e., immortal), and with the capability to differentiate into all three germ layers (e.g., endoderm, mesoderm and ectoderm). Further techniques to characterize the pluripotency of a given population of cells include injection into an immunocompromised animal, such as a severe combined immunodeficient ("SCID") mouse, for formation of teratomas containing cells or tissues characteristic of all three germ layers.

Described herein is a composition of induced pluripotent stem cells ("iPSCs"). In one embodiment, the method of generating induced pluripotent stem cells, includes providing a quantity of somatic or non-embryonic cells, contacting the somatic or non-embryonic cells with a quantity of one or more reprogramming factors and one or more RNA molecules, and culturing the somatic or non-embryonic cells for a period of time sufficient to generate at least one induced pluripotent stem cell. In other embodiments, this includes culturing the cells in a reprogramming media for at least 1, 2, 3, 4, 5, 6, or 7 days. In other embodiments, this includes further culturing the somatic cell or non-embryonic cell in an induction media for at least 1, 2, 3, 4, 5, 6, 7, 8, 9, or 10 days. In other embodiments, the culturing the cells in a reprogramming media is for 8-14 days. In other embodiments, further culturing the cells in an induction media is for 1-12 days. In other embodiments, the culturing the cells in a reprogramming media is for 8-14 days and further culturing the cells in an induction media is for 1-12 days.

In certain embodiments, the composition of induced pluripotent stem cells generated by the described methods is substantially free of viral proteins and/or exogenously delivered DNA. This can include cells generated by a method including contacting the somatic or non-embryonic cells with a quantity of reprogramming factors and one or more RNA molecules via a non-integrative delivery platform to a somatic cell or non-embryonic cell. In other embodiments, this includes culturing the cells in a reprogramming media for at least 1, 2, 3, 4, 5, 6, or 7 days. In other embodiments, this includes further culturing the somatic cell or non-embryonic cell in an induction media for at least 1, 2, 3, 4, 5, 6, 7, 8, 9, or 10 days.

In various embodiments, providing a quantity of somatic or non-embryonic cells, contacting the somatic or non-embryonic cells with a quantity of one or more reprogramming factors and one or more RNA molecules, culturing and/or further culturing generates a composition of induced pluripotent stem cells substantially free of viral proteins and/or exogenously delivered DNA. In certain embodiments, the one or more reprogramming factors includes Oct-4, Sox-2, Klf-4, c-Myc (1-Myc), Lin-28, SV40 Large T Antigen ("SV40LT"), Sall4, Fbx-15, Utf-1, Tert, and/or short hairpin RNAs targeting p53 ("shRNA-p53"). In certain embodiments, the one or more reprogramming factors are Oct-4, Sox-2, Klf-4, and c-Myc. In other embodiments, the RNA molecules are microRNAs. In other embodiments, the one or more microRNAs includes microRNAs readily ascertainable to one of ordinary skill. For example, a microRNA registry is provided by the University of California, Santa Cruz Human Genome Database (http://genome.ucsc.edu). In certain embodiments, the microRNAs can include, miR-106a, miR-106b, miR-106b-25 miR-20b, miR-93, miR-17, miR-291a, miR-291b-5p, miR-294, miR-295, miR-302a, miR-302b, miR-302c, miR-302d, miR-25, miR-32, miR-92a-1, miR-92a-2, miR-92b, miR-363, miR-367, miR-19a, miR-19b, miR-290-5p, miR-292, miR-200c, miR-20a, miR-290-3p, miR-18b, miR-291b-3p, miR-293, miR-363 and/or miR-369-5p, derivatives and orthologs thereof. In other embodiments, the microRNAs include least one miR-302 cluster member, at least one miR-367 cluster member, and at least one miR-200 cluster member. In other embodiments, the one or more microRNAs are miR-302a, miR-302b, miR-302c, miR-302d, miR-367, and miR-200c. In other embodiments, the one or more microRNAs are miR-302, miR-200c, miR-106a, miR-106b-25, and miR-363, including combinations such as miR-302+miR-200c+miR-106a/miR-363 or miR-302+miR-200c+miR-106b-25. In other embodiments, the one or more reprogramming factors are Oct-4, Sox-2, Klf-4, and c-Myc and the one or more RNA molecules are miR-302a, miR-302b, miR-302c, miR-302d, miR-367, and miR-200c microRNAs. In other embodiments, the one or more reprogramming factors are Oct-4, Sox-2, Klf-4, and c-Myc (1-Myc) and the one or more RNA molecules are miR-302, miR-200c, miR-106a, miR-106b-25, and miR-363 microRNAs. In various embodiments, the somatic cell or non-embryonic cell is from a primate. In various embodiments, the somatic cell or non-embryonic cell is from a human.

In other embodiments, the one or more reprogramming factors are encoded in a combination of one or more viruses. In other embodiments, one or more reprogramming factors are encoded in a combination of one or more non-integrative viruses. In certain embodiments, the non-integrative virus is an Adenovirus-based or Sendai-based virus. In other embodiments, one or more reprogramming factors are encoded in a combination of one or more vectors. In certain embodiments, the vector is an episomal or minicircle vector. In certain embodiments, the episomal vector is oriP/Nuclear Antigen-1 vector. In other embodiments, one or more RNA molecules are encoded in a combination of one or more viruses. In other embodiments, the RNA molecules are microRNAs. In other embodiments, one or more microRNAs are encoded in a combination of one or more viruses. In other embodiments, one or more microRNAs are encoded in a combination of one or more non-integrative viruses. In certain embodiments, the non-integrative virus is an Adenovirus-based or Sendai-based virus. In other embodiments, one or more microRNAs are encoded in a combination of one or more vectors. In certain embodiments, the vector is an episomal or minicircle vector. In certain embodiments, the episomal vector is oriP/Nuclear Antigen-1 vector. In various embodiments, the microRNA is encoded as an immature RNA sequence that is processed into a 18, 19, 20, 21, 22, 23, 24, 25, 26 or more nucleotide microRNA following interaction with a member of the RNAi silencing complex ("RISC"), such as Dicer and Argonaut.

In certain other embodiments, the reprogramming media includes one or more induction, such as PD0325901, CHIR99021, HA-100, A-83-01, valproic acid ("VPA"), SB431542, and/or Rho-associated coiled-coil-containing protein kinase ("ROCK") inhibitors, such as Y-27632 and thiazovivin ("Tzv")

In other embodiments, the one or more reprogramming factors and one or more microRNAs are exogenously delivered by techniques known in the art, such as nuclefection, transfection, transduction, electrofusion, electroporation, microinjection, cell fusion, among others. In other embodiments, the reprogramming factors are provided as RNA, linear DNA, peptides or proteins, or a cellular extract of a pluripotent stem cell.

In different embodiments, culturing the cells in a reprogramming media is for at least 7, 8, 9, 10, 11, 12, 13, 14, 15, or 16 days. In different embodiments, culturing the cells in a reprogramming media is for at least 7, 8, 9, 10, 11, 12, 13, 14, 15, or 16 days. In different embodiments, culturing the cells in an induction media is for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In other embodiments, the culturing the cells in a reprogramming media is for 8-14 days. In other embodiments, further culturing the cells in an induction media is for 1-12 days. In other embodiments, the culturing the cells in a reprogramming media is for 8-14 days and further culturing the cells in an induction media is for 1-12 days.

In different embodiments, the method further includes isolating at least one induced pluripotent stem cell. Further described herein is a cell line including induced pluripotent stem cells generated by the described methods, wherein the cell line includes cells substantially free of exogenous DNA. Also described herein is a pharmaceutical composition including a quantity induced pluripotent stem cells generated by the described methods and a pharmaceutically acceptable carrier. Also described herein is n induced pluripotent stem cell line substantially free of exogenous DNA.

In various embodiments, the iPSCs and iPSCs produced by the described methods possess features of pluripotent stem cells. Some exemplary features of pluripotent stem cells including differentiation into cells of all three germ layers (ectoderm, endoderm, mesoderm), either in vitro or in vivo when injected into an immunodeficient animal, expression of pluripotency markers such as Oct-4, Sox-2, nanog, TRA-1-60, TRA-1-81, S SEA-4, high levels of alkaline phosphatase ("AP") expression, indefinite propagation in culture, among other features recognized and appreciated by one of ordinary skill.

Other embodiments include a pharmaceutical composition including a quantity of iPSCs generated by the above described methods, and a pharmaceutically acceptable carrier.

Also described herein is an efficient method for generating induced pluripotent stem cells, including providing a quantity of cells, contacting the somatic or non-embryonic cells with a quantity of one or more reprogramming factors and one or more RNA molecules, and culturing the somatic or non-embryonic cells for a period of time sufficient to generate at least one induced pluripotent stem cell. In other embodiments, culturing the cells in a reprogramming media is for at least 7 days, and further culturing the cells in an induction media is for at least 10 days. In other embodiments, the culturing the cells in a reprogramming media is for 8-14 days and further culturing the cells in an induction media is for 1-12 days. In various embodiments, providing a quantity of somatic or non-embryonic cells, contacting the somatic or non-embryonic cells with a quantity of one or more reprogramming factors and one or more RNA molecules, culturing and/or further culturing generates a composition of induced pluripotent stem cells substantially free of viral proteins and/or exogenously delivered DNA. In other embodiments, the RNA molecules are microRNAs.

In certain embodiments, the one or more reprogramming factors includes Oct-4, Sox-2, K1f-4, c-Myc (or 1-Myc), Lin-28, SV40LT, Sal14, Fbx-15, Utf-1, Tert, and/or shRNA-p53. In certain embodiments, the one or more reprogramming factors are Oct-4, Sox-2, Klf-4, and c-Myc (or 1-Myc). In other embodiments, the one of more microRNAs can miR-106a, miR-106b, miR-106b-25 miR-20b, miR-93, miR-17, miR-291a, miR-291b-5p, miR-294, miR-295, miR-302a, miR-302b, miR-302c, miR-302d, miR-25, miR-32, miR-92a-1, miR-92a-2, miR-92b, miR-363, miR-367, miR-19a, miR-19b, miR-290-5p, miR-292, miR-200c, miR-20a, miR-290-3p, miR-18b, miR-291b-3p, miR-293, miR-363 and/or miR-369-5p, derivatives and orthologs thereof. In other embodiments, the microRNAs include least one miR-302 cluster member, at least one miR-367 cluster member, and at least one miR-200 cluster member. In other embodiments, the one or more microRNAs are miR-302a, miR-302b, miR-302c, miR-302d, miR-367, and miR-200c. In other embodiments, the one or more microRNAs are miR-302, miR-200c, miR-106a, miR-106b-25, and miR-363, including combinations such as miR-302+miR-200c+miR-106a/miR-363 or miR-302+miR-200c+miR-106b-25. In other embodiments, the one or more reprogramming factors are Oct-4, Sox-2, Klf-4, and c-Myc (or 1-Myc) and the one or more RNA molecules are miR-302a, miR-302b, miR-302c, miR-302d, miR-367, and miR-200c microRNAs. In other embodiments, the one or more reprogramming factors are Oct-4, Sox-2, Klf-4, and c-Myc (or 1-Myc) and the one or more RNA molecules are miR-302, miR-200c, miR-106a, miR-106b-25, and miR-363 microRNAs. In various embodiments, the somatic cell or non-embryonic cell is from a primate. In various embodiments, the somatic cell or non-embryonic cell is from a human.

In certain other embodiments, the reprogramming media includes PD0325901, CHIR99021, HA-100, A-83-01, VPA, SB431542, a ROCK inhibitor, such as Y-27632 and Tzv.

In other embodiments, the reprogramming factors are delivered by techniques known in the art, such as nucleofection, transfection, transduction, electrofusion, electroporation, microinjection, cell fusion, among others. In other embodiments, the reprogramming factors are provided as RNA, linear DNA, peptides or proteins, or a cellular extract of a pluripotent stem cell. In certain embodiments, the cells are treated with sodium butyrate prior to delivery of the reprogramming factors. In other embodiments, the cells are incubated or 1, 2, 3, 4, or more days on a tissue culture surface before further culturing. This can include, for example, incubation on a Matrigel coated tissue culture surface. In other embodiments, the reprogramming conditions include application of norm-oxygen conditions, such as 5% $O_2$, which is less than atmospheric 21% $O_2$. In certain embodiments, the induction media is a chemically defined, serum-free media.

Efficiency of reprogramming is readily ascertained by one of many techniques readily understood by one of ordinary skill. For example, efficiency can be described by the ratio between the number of donor cells receiving the full set of reprogramming factors and the number of reprogrammed colonies generated. Measuring the number donor cells receiving reprogramming factors can be measured directly, when a reporter gene such as GFP is included in a vector encoding a reprogramming factor. Alternatively, indirect measurement of delivery efficiency can be provided by transfecting a vector encoding a reporter gene as a proxy to gauge delivery efficiency in paired samples delivering reprogramming factor vectors. Further, the number of reprogrammed colonies generated can be measured by, for example, observing the appearance of one or more embryonic stem cell-like pluripotency characteristics such as alkaline phosphatase (AP)-positive clones, colonies with endogenous expression of transcription factors Oct-4 or nanog, or antibody staining of surface markers such as Tra-1-60. In another example, efficiency can be described by the kinetics of induced pluripotent stem cell generation.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

The present invention may be as defined in any one of the following numbered paragraphs.

1. A method of generating induced pluripotent stem cells, comprising:
   providing a quantity of somatic or non-embryonic cells;
   contacting the somatic or non-embryonic cells with a quantity of one or more reprogramming factors and one or more RNA molecules;
   culturing the somatic or non-embryonic cells for a period of time sufficient to generate at least one induced pluripotent stem cell.
2. The method of paragraph 1, wherein contacting the cells with a quantity of the one or more reprogramming factors and one or more RNA molecules comprises transduction, nucleofection, electroporation, direct injection and/or transfection.
3. The method of paragraph 1, wherein the one or more reprogramming factors comprise one or more factors selected from the group consisting of: Oct-4, Sox-2, Klf-4, c-Myc, Lin-28, SV40 Large T Antigen ("SV40LT"), and short hairpin RNAs targeting p53 ("shRNA-p53").
4. The method of paragraph 3, wherein the one or more reprogramming factors are Oct-4, Sox-2, Klf-4, and c-Myc.
5. The method of paragraph 1, wherein the one or more RNA molecules are microRNAs.
6. The method of paragraph 5, wherein the microRNAs comprise miR-106a, miR-106b, miR-106b25, miR-20b, miR-93, miR-17, miR-291a, miR-291b-5p, miR-294, miR-295, miR-302a, miR-302b, miR-302c, miR-302d, miR-25, miR-32, miR92a-1, miR92a-2, miR92b, miR-363, miR-367, miR-19a, miR-19b, miR-290-5p, miR-292, miR-200c, miR-20a, miR-290-3p, miR-18b, miR-291b-3p, miR-293, and/or miR-369-5p, derivatives and orthologs thereof.
7. The method of paragraph 5, wherein the microRNAs comprise at least one miR-302 cluster member, at least one miR-367 cluster member, and at least one miR-200 cluster member.
8. The method of paragraph 5, wherein the one or more microRNAs are miR-106a, miR-106b-25 miR-302a, miR-302b, miR-302c, miR-302d, miR-363, miR-367, and miR-200c.
9. The method of paragraph 1, wherein the one or more reprogramming factors are Oct-4, Sox-2, Klf-4, and c-Myc and the one or more RNA molecules are miR-106a, miR-106b-25 miR-302a, miR-302b, miR-302c, miR-302d, miR-363, miR-367, and miR-200c microRNAs.
10. The method of paragraph 1, wherein the one or more reprogramming factors and one or more RNA molecules are encoded in one or more viruses.
11. The method of paragraph 10, wherein the one or more viruses are non-integrative viruses.
12. The method of paragraph 11, wherein the non-integrative virus is an Adenovirus or Sendai virus.
13. The method of paragraph 1, wherein the one or more reprogramming factors and one or more RNA molecules are encoded in one or more non-integrative vectors.
14. The method of paragraph 13, wherein the non-integrative vector is an episomal or minicircle vector.
15. The method of paragraph 1, wherein the reprogramming media comprises at least one chemical induction molecule.
16. The method of paragraph 1, wherein the reprogramming media comprises culturing the somatic or non-embryonic cells in a reprogramming media for at least 7 days; and
17. The method of paragraph 1, wherein culturing the somatic or non-embryonic cells in a reprogramming media is for at least 7, 8, 9, 10, 11, 12, 13, 14, 15, or 16 days.
19. The method of paragraph 1, wherein culturing the somatic or non-embryonic cells in a reprogramming media is for 8 to 14 days.
20. The method of paragraph 1, wherein generating induced pluripotent stem cells comprises further culturing the somatic or non-embryonic cells in an induction media for at least 10 days.
21. The method of paragraph 1, wherein further culturing the somatic or non-embryonic cells in an induction media is for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

22. The method of paragraph 1, wherein further culturing the somatic or non-embryonic cells in an induction media is for 1 to 12 days.

23. The method of paragraph 1, wherein the induction media is a serum-free media.

24. The method of any one of paragraphs 1-23, further comprising isolating at least one induced pluripotent stem cell.

25. A cell line comprising induced pluripotent stem cells generated by the method of any one of paragraphs 1-24, wherein the cell line comprises cells substantially free of exogenous DNA.

26. A pharmaceutical composition comprising:
a quantity induced pluripotent stem cells generated by the method of any one of paragraphs 1-24; and
a pharmaceutically acceptable carrier.

27. An induced pluripotent stem cell line substantially free of exogenous DNA.

The invention is further illustrated by the following examples, which should not be construed as further limiting.

EXAMPLES

Example 1

Figure 2:
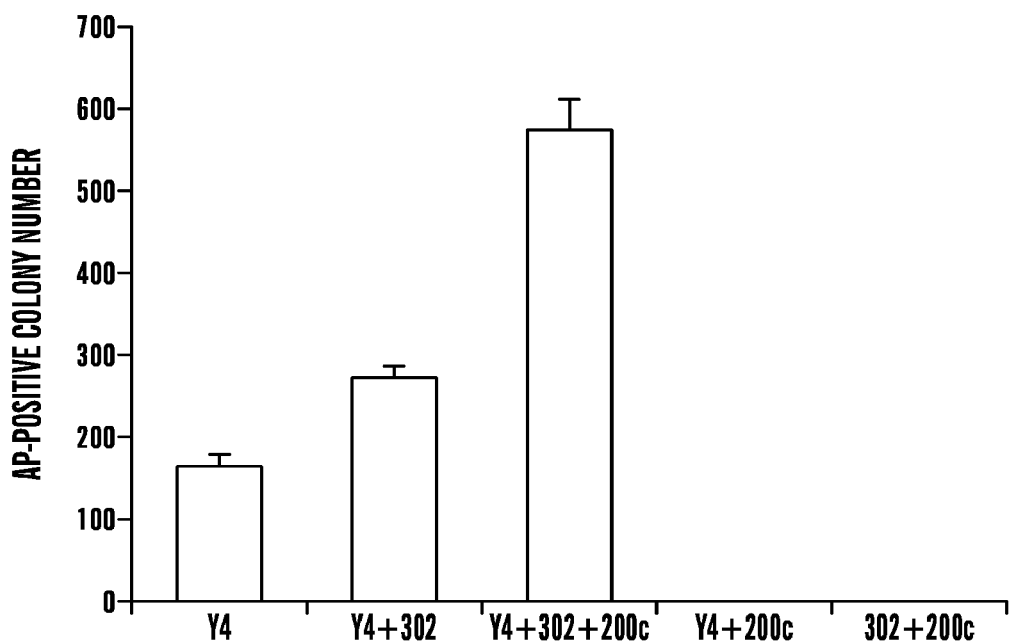
FIG. 2 shows experimental results that indicate a synergistic effect of reprogramming transcription factors and microRNAs. Human fibroblasts (Nuff) were transduced with lentiviral vectors expressing the Yamanaka factors Oct-4, Sox-2, c-Myc and Klf-4 ("Y4") and/or microRNAs (note: "302" denotes contains microRNAs from both the miR-302 and miR-367 clusters). The number of iPSC-like colonies (alkaline phosphatase-positive) were counted at 14 days as a measurement of pluripotency.

Requirement of Reprogramming Factors for iPSC Generation—Synergistic Effects with MicroRNAs Using the described methods incorporating both reprogramming transcription factors and microRNAs, human fibroblasts (Nuff) were transduced with lentiviral vectors expressing the Yamanaka factors Oct-4, Sox-2, c-Myc and Klf-4 ("Y4") and each of potential microRNAs (106a/363, 106b-25, 136s, 17/92, 302s, 369s, and 371/73) that are implicated in the control of pluripotency. The number of iPSC-like colonies (alkaline phosphatase-positive) were counted at 14 days as a measurement of pluripotency. As shown in FIG. 1(b), addition of miRNA 302s, 106a/363 or 106b-25 significantly increased the number of iPSC-like colonies, suggesting that these miRNAs facilitate the reprogramming process. Among these, microRNA 302s/367 exhibited the strongest effect. Thus, the combination of microRNA302s/367 and each of other microRNAs were tested. Human fibroblasts (Nuff) were next transduced with lentiviral vectors expressing the Yamanaka factors ("Y4" which includes Oct-4, Sox-2, c-Myc (or 1-Myc) and Klf-4) and/or microRNAs selected either from miR-302s/367 with or without miR-200c, as shown (note: "302" denotes contains microRNAs from both the miR-302 and miR-367 clusters). Importantly, delivery of microRNAs alone failed to result in any measurable reprogramming, and miR-302s/367 in combination with Y4 factors were required, as shown in FIG. 2. The combination of Y4 and miR-200c also failed to result in any measurable reprogramming. Remarkably, the full slate of Y4, miR-302s/367 and miR-200c provided a powerful synergistic effect, at approximately 4× the efficiency of using the Y4 reprogramming factors alone. The synergistic effect of microRNAs is further demonstrated by the apparent incapacity of miR-200c to enhance reprogramming with Y4, yet miR-200c addition provides nearly a 2× increase in efficiency when used in combination with Y4 miR-302s/367. The number of iPSC-like colonies were measured by assaying alkaline phosphatase, a pluripotency marker, as counted 14 days following transfection.

Example 2

Effectiveness of iPSC Reprogramming Enhanced by Combinations of microRNAs I

Figure 3:
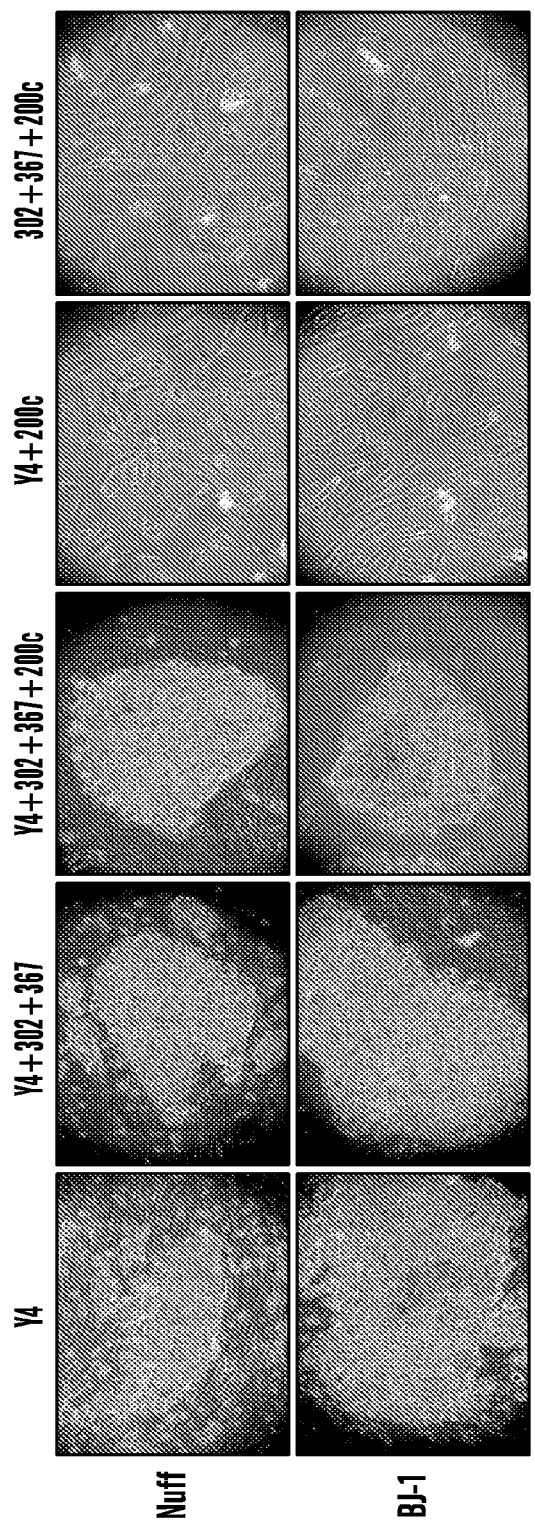
FIG. 3 shows experimental results that indicate successful reprogramming of fibroblasts into iPSCs. Fully reprogrammed iPSCs with human ESC-like morphology were generated when Y4F and miR-302+367+200c clusters were used in combination using lentiviral vectors in both fibroblasts Nuff And BJ-1 cell lines. When only microRNAs were used, human iPSCs were not generated. As expected, reprogramming transcription factors Y4F generated many reprogrammed colonies. Interestingly, combined use of miR-200c cluster inhibited iPSC generation by Y4F. Further, when Y4F and miR-302+367+200c clusters were used, hiPSC colonies were morphologically more similar to typical hESC colonies.

Fully reprogrammed iPSCs with human ESC-like morphology were generated when Y4F and miR-302+367+200c clusters were used in combination using lentiviral vectors in both fibroblasts Nuff and hTERtBJ-1 cell lines, as shown in Figure. 3. When only microRNAs were used, human iPSCs were not generated. As expected, Y4F generated many reprogrammed colonies. Interestingly, combined use of miR-200c cluster inhibited iPSC generation by Y4F. Interestingly, when Y4F and miR-302+367+200c clusters were used, human iPSC colonies were morphologically more similar to typical human ESC colonies from the first time.

Example 3

Effectiveness of iPSC Reprogramming Enhanced by Combinations of microRNAs II

Figure 4A:
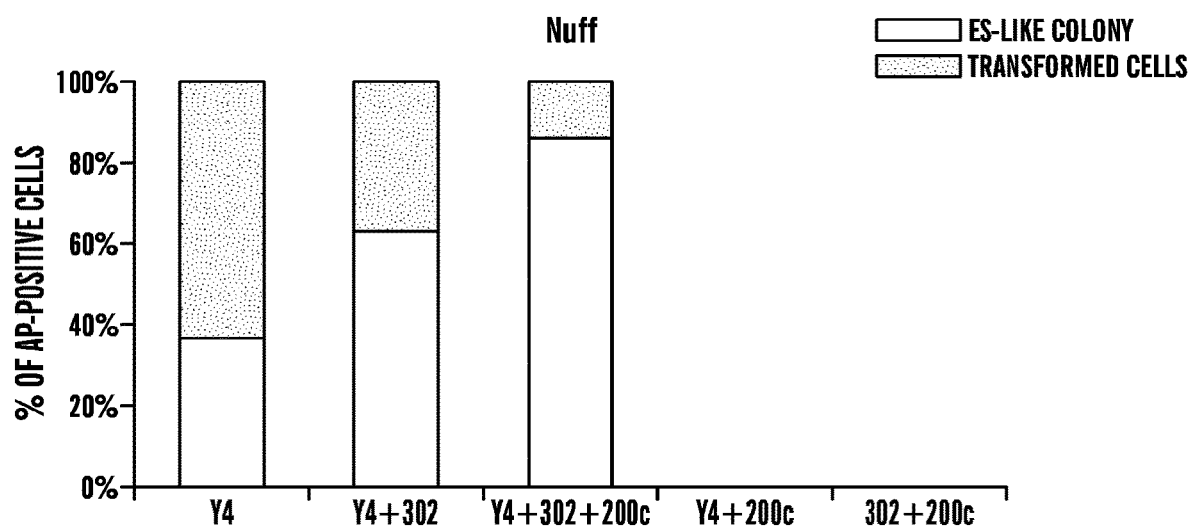
FIG. 4A-FIG. 4B shows experimental results that indicate enhanced morphological similarity of iPSCs cells when adding microRNAs to reprogramming transcription factors. Morphological analyses of iPSC-like and transformed colonies at 14 days. When only Y4F were expressed, many colonies were transformed colonies without human ESC-like morphology. However, when Y4F and microRNA 302+367+200c clusters were used in combination, most colonies exhibited more genuine human ESC-like morphology. Distribution across alkaline phosphatase-positive cells is shown for (A) Nuff and (B) BJ-1 cell lines.
Figure 4B:
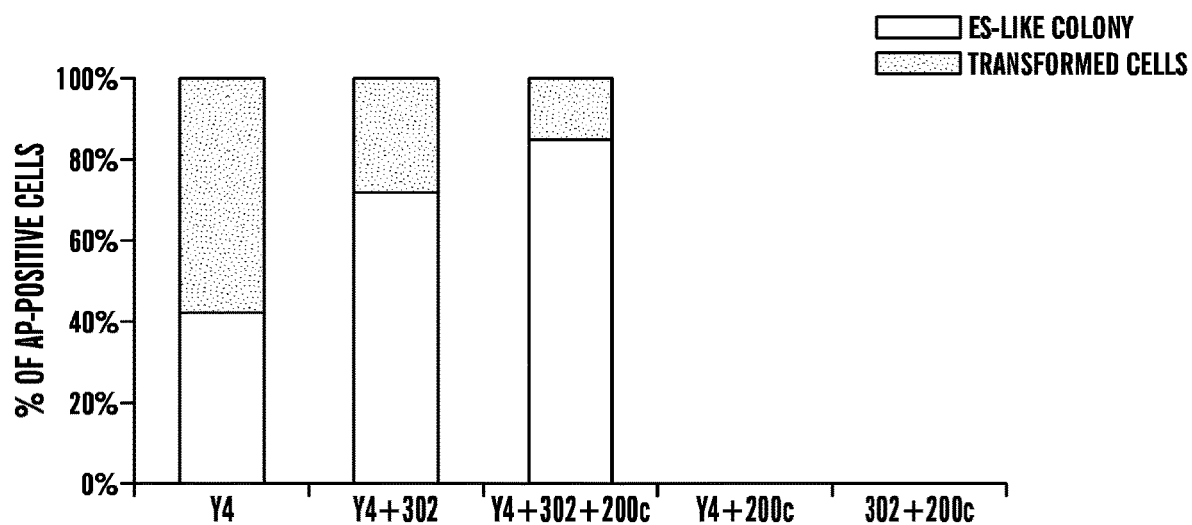

Morphological analyses of iPSC-like and transformed colonies at 14 days. When only Y4F were expressed, many colonies were transformed colonies without human ESC-like morphology, as shown in FIG. 4. However, when Y4F and microRNA 302+367+200c clusters were used in combination, most colonies exhibited more genuine human ESC-like morphology. These results were reproducible in both (A) Nuff and (B) BJ-1 cell lines, as shown.

Example 4

Effectiveness of iPSC Reprogramming Enhanced by Combinations of microRNAs III

Figure 5:
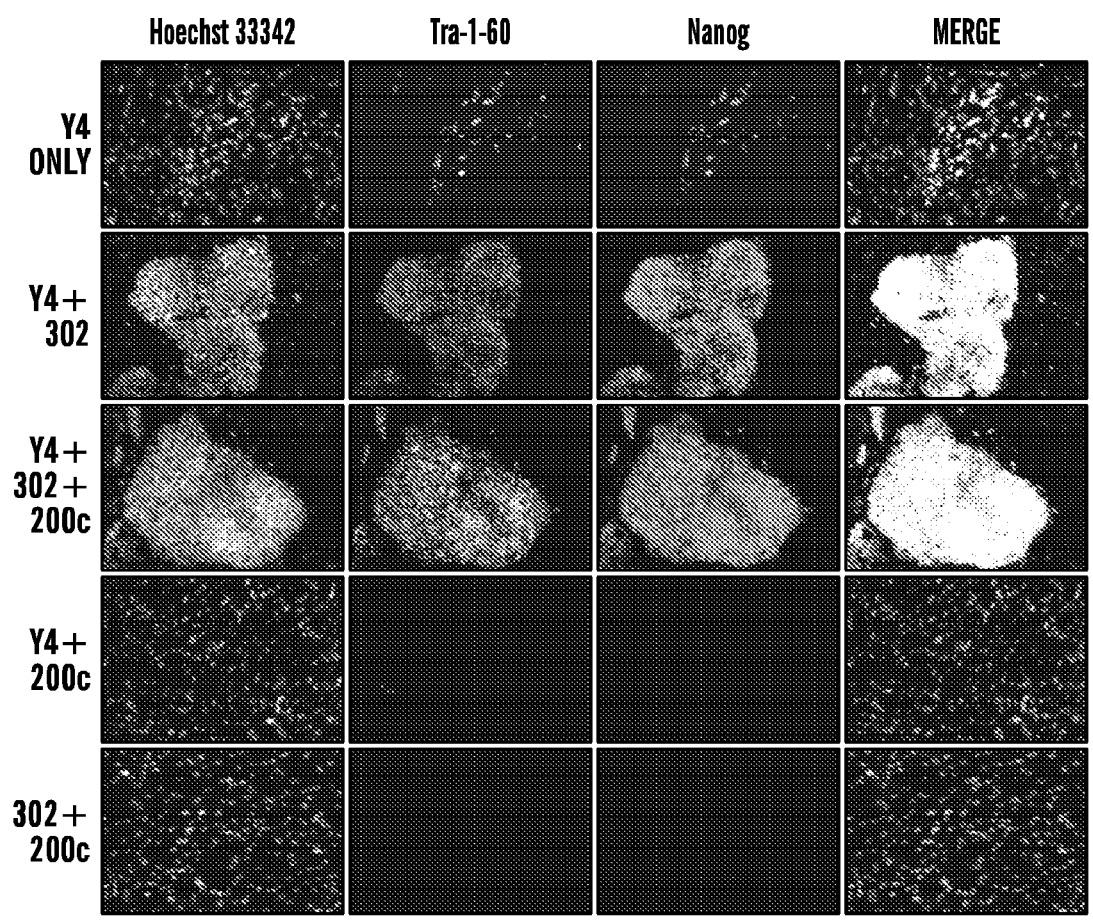
FIG. 5 shows experimental results that indicate enhanced speed of reprogramming using reprogramming transcription factors and microRNAs. Morphological analyses at dl 4 show that iPSCs are generated much faster when Y4F and microRNA 302+367+200c clusters were used in combination, as shown by the acquisition of pluripotent marker Nanog, and surface antigen marker Tra-1-60. In contrast, when only Y4F were expressed, iPSC-like colonies were not formed yet. In addition, no colonies were formed when microRNAs only were expressed.

Morphological analyses at d14 show that iPSCs are generated much faster when Y4F and microRNA 302+367+200c clusters were used in combination, as shown in FIG. 5. In contrast, when only Y4F were expressed, iPSC-like colonies were not formed yet. In addition, no colonies were formed when microRNAs only were expressed.

Example 5

Figure 7A:
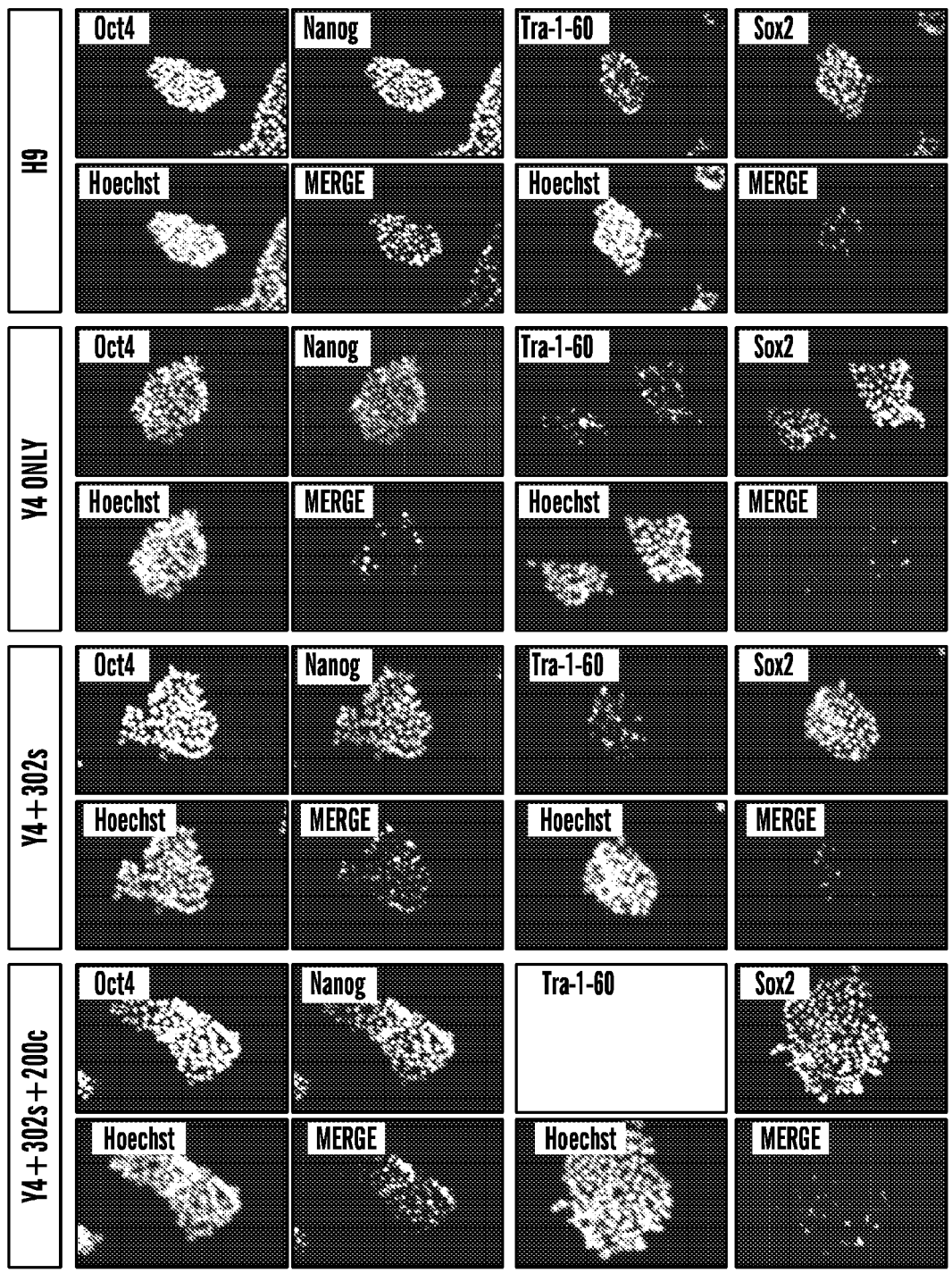
FIG. 7A-FIG. 7B shows experimental results that indicate characterization of Epi-iPSC clones generated by episomal vector-based reprogramming transcription factors and microRNAs. (A) Immunostaining analyses for pluripotent cell markers Oct4, Nanog, and Sox2, and surface antigen marker Tra-1-60. (B) Real time RT-PCR analyses for pluripotent cell markers. Total RNA was isolated from Epi-iPSC clones established with the combination of Y4F and microRNA 302s±200c, from human ESC (H9), and from BJ cell lines.
Figure 7B:
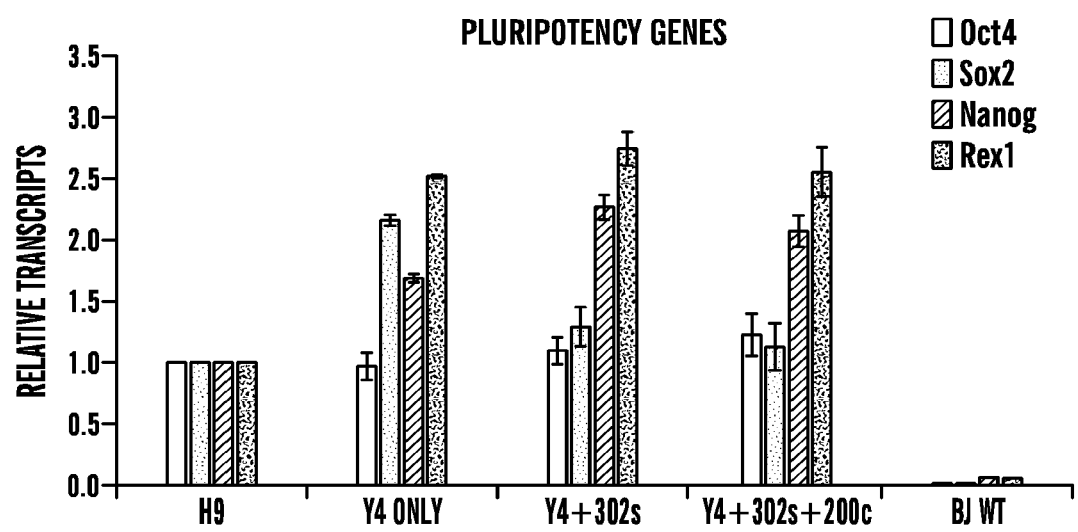
Figure 8A:
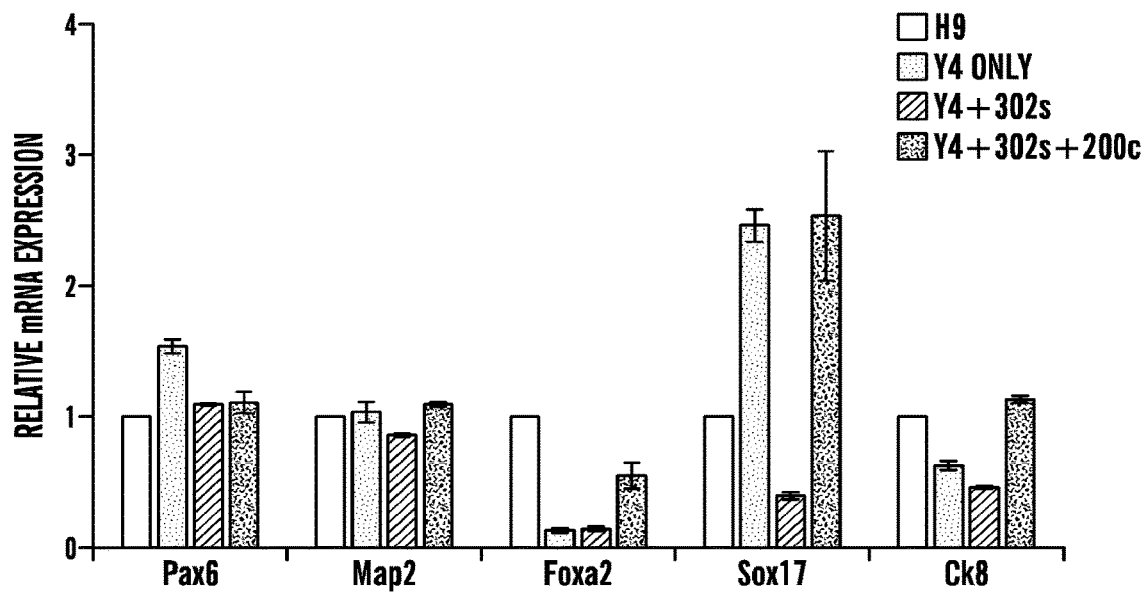
FIG. 8A-FIG. 8E shows experimental results that indicate in vitro differentiation of Epi-iPSC clones. Epi-iPSCs were in vitro differentiated for 7 days, and analyzed for expression of markers representing mesoderm (A) and ectoderm and endoderm (B) by realtime RT-PCR analyses. The expression level of each gene was shown as relative value following normalization against that of the glyceraldehyde 3-phosphate dehydrogenase (Gapdh) gene. In addition, in vitro differentiated cells from Epi-iPSCs for 7 days were immunostained with the mesoderm marker Brachyury (C), ectoderm marker Otx2 (D) or endoderm marker Sox17 (E).
Figure 8B:
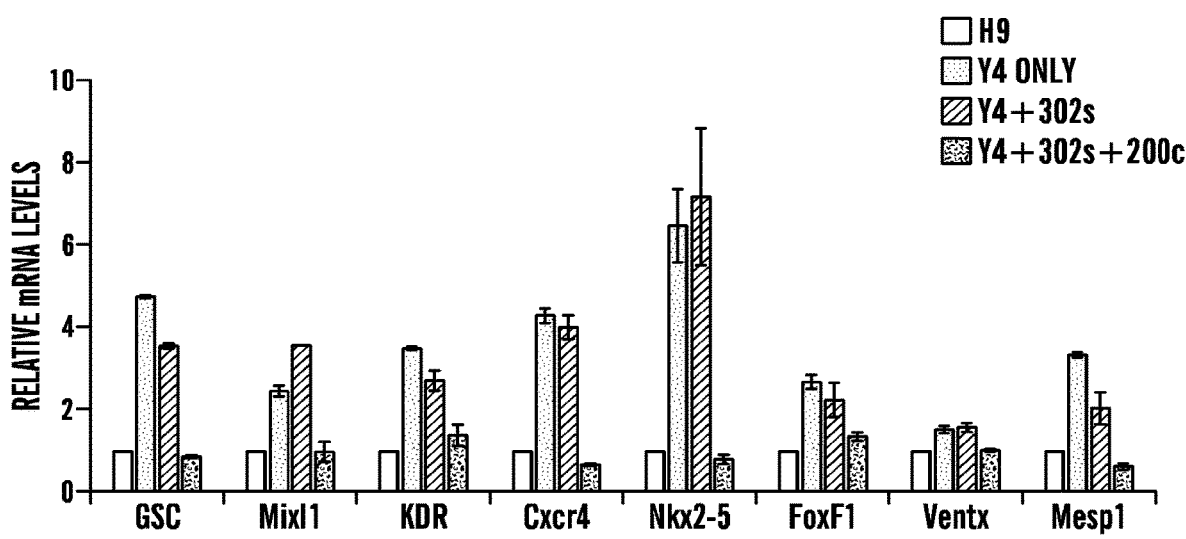
Figure 8C:
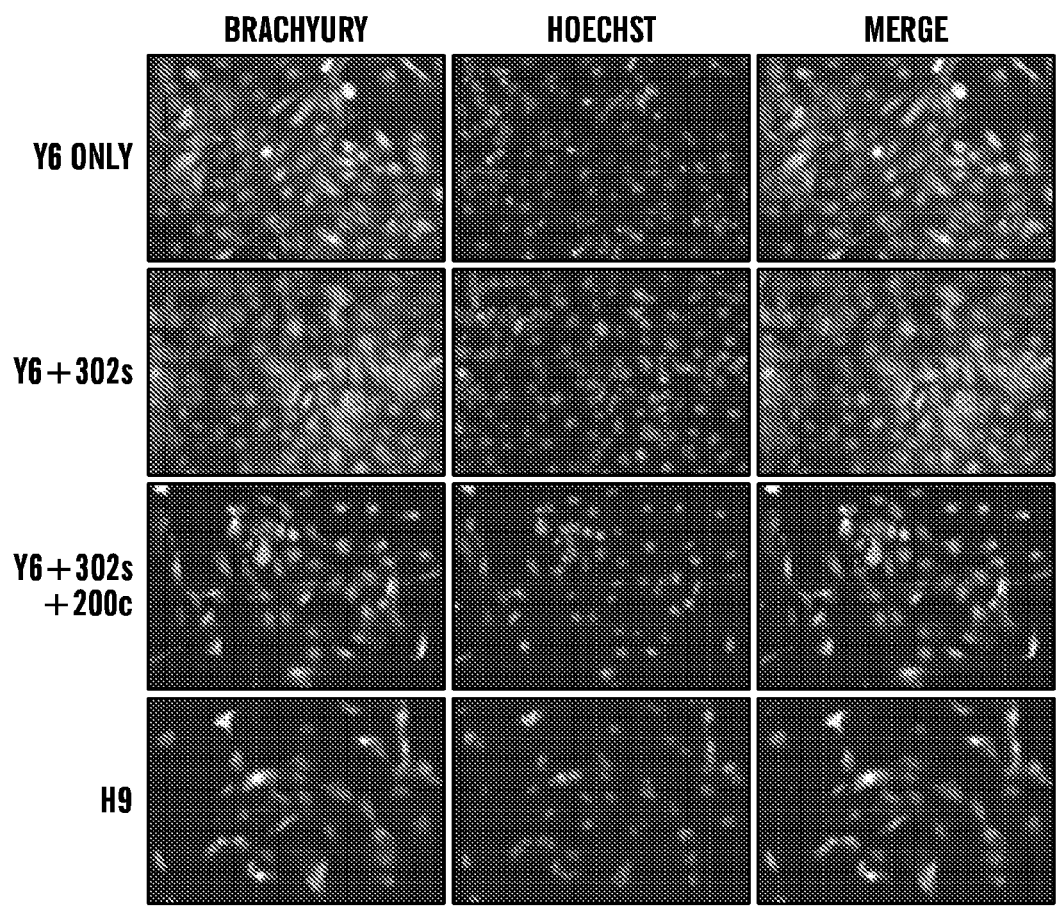
Figure 8D:
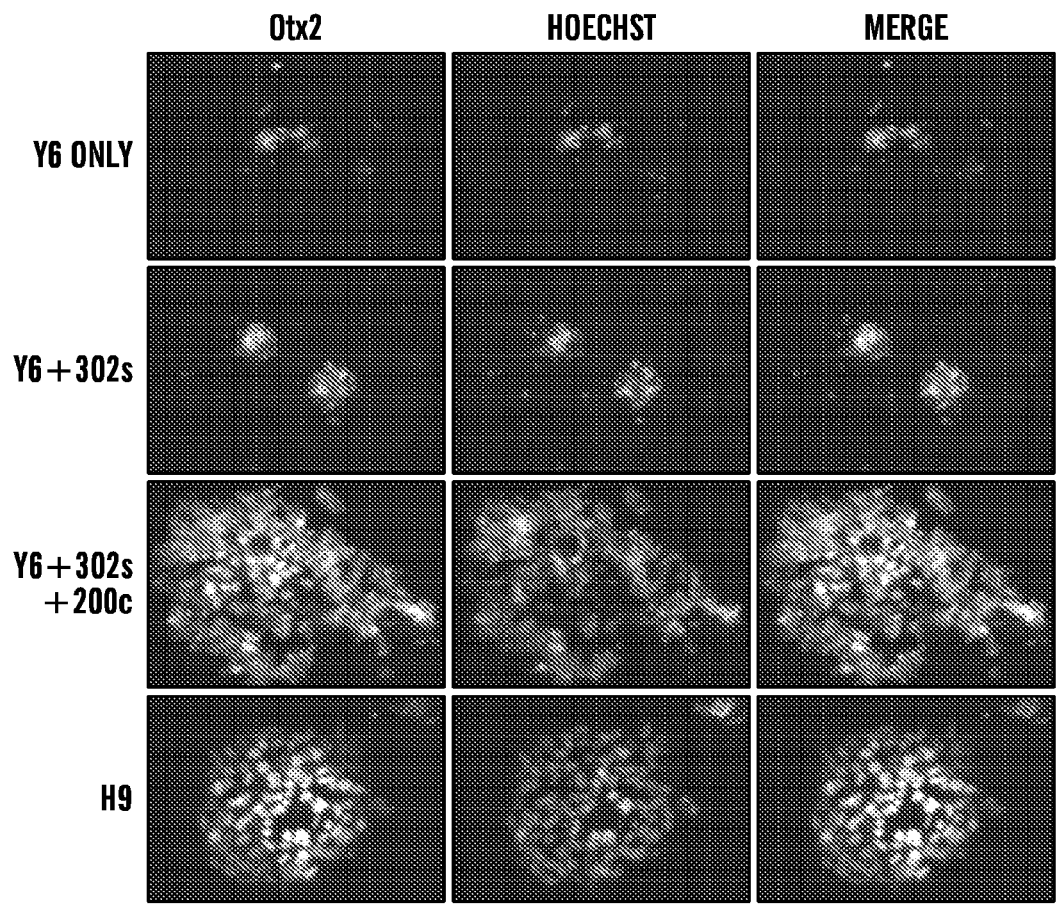
Figure 8E:
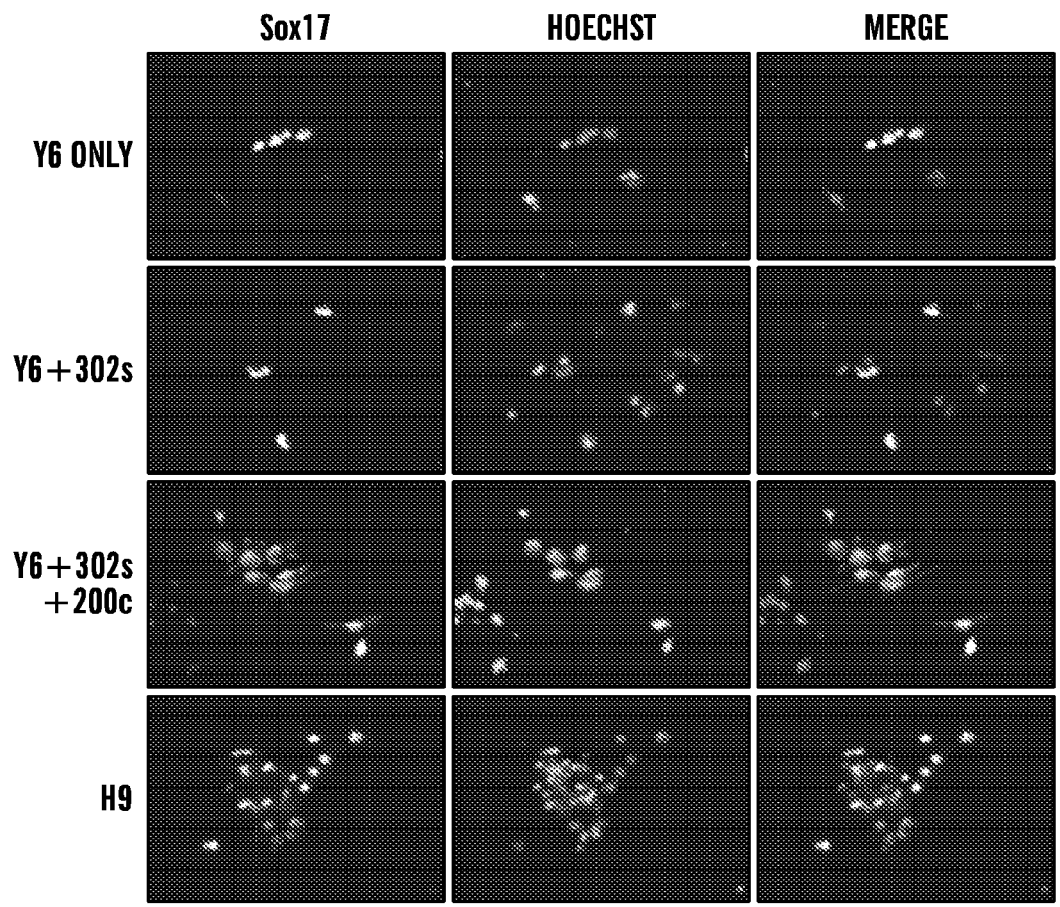
Figure 9:
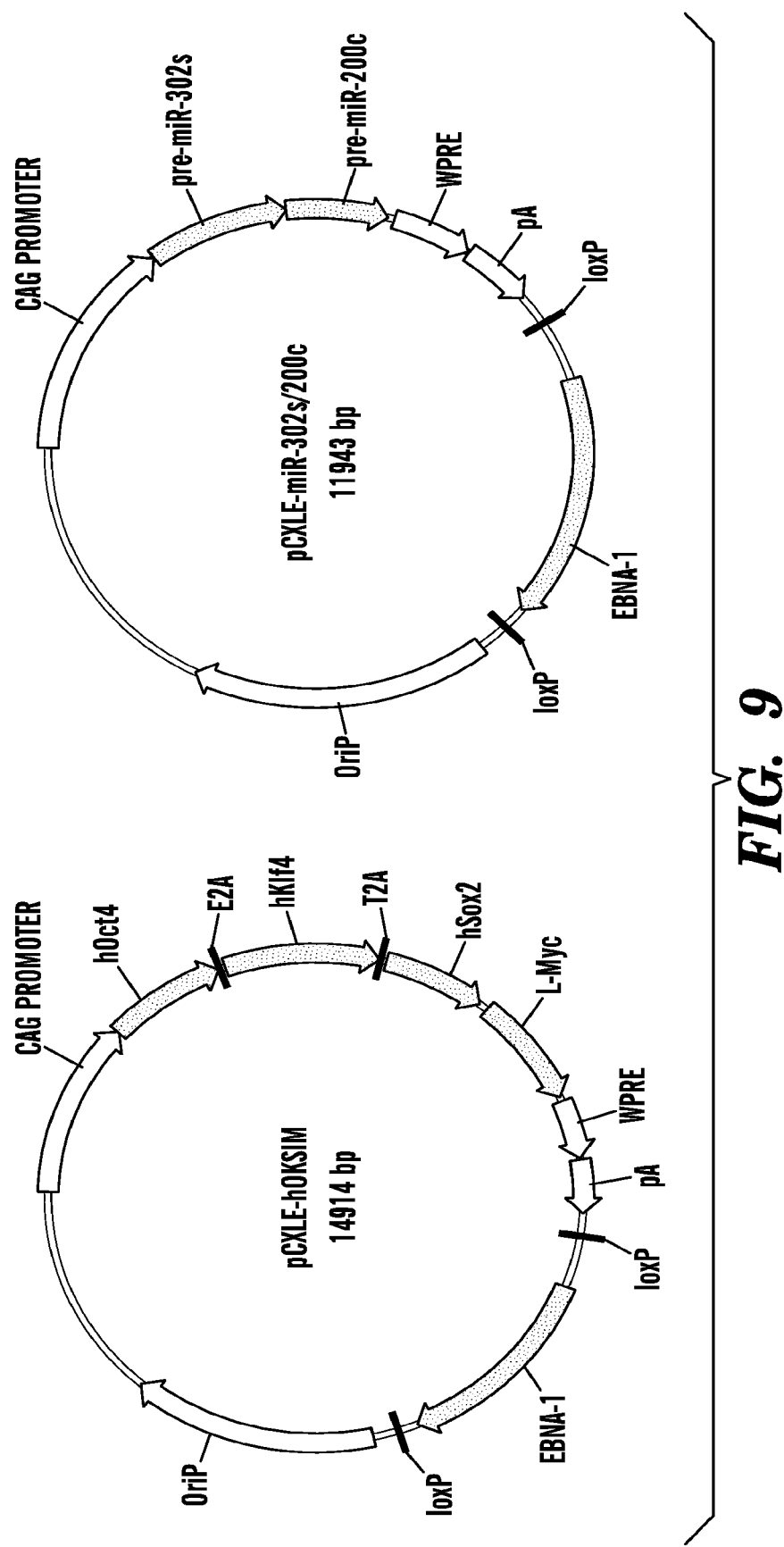
FIG. 9 shows schematic diagrams of two episomal expression vectors, pCXLE-hOKS1M and pCXLE-miR-302s/200c. pCXLE-hOKS1M expresses Y4 factors (Oct4, Klf4, Sox2 and L-Myc) while pCXLE-miR-302s/200c expresses microRNA clusters 302s and 200c. CAG, CAG promoter; WPRE, woodchuck hepatitis post-transcriptional regulatory element; and pA, polyadenylation signal.

Characterization of iPSC Clones Generated by Combined Expression of Y4 and microRNAs I In order to determine whether the Epi-iPSCs have hESC-like properties, the inventors examined them for expression of pluripotent markers, including Oct4, Sox2, Nanog, and Rex1. Morphological analyses (A) for pluripotent markers Oct4, Nanog, and Sox2, and Tra-1-60 and quantitative reverse transcription PCR (qRT-PCR) analyses (B) show that those iPSC clones prominently expressed the pluripotent markers including Oct3, Sox2, Nanog, and Rex1 under undifferentiated condition, as shown in FIG. 7.

Example 6

Characterization of iPSC Clones Generated by Combined Expression of Y4 and microRNAs II To investigate the differentiation potential of Epi-iPSCs, in vitro differentiation was induced for 7 days by removing basic FGF and adding ITSFn medium to iPSC clones. Interestingly, Y4+302s+200c-induced iPSC clones differentiated into lineage cells expressing three germ layers, as shown in FIG. 8. In contrast, the great majority of mesoderm marker genes were markedly activated, whereas ectoderm and endoderm markers were decreased in Y4– or Y4+302s-iPSC clones compared to H9 cells, as shown.

Example 7

Summary of Synergistic Effects Provided by microRNAs in Reprogramming

Using the Yamanaka four factors (Y4: Oct-4, Sox-2, Klf-4, and c-Myc (or 1-Myc), the Inventors could generate many iPSC-like colonies. Surprisingly, addition of one of pluripotency-related microRNAs (miR-200c cluster) completely abolished generation of iPSCs. Addition of miR-302 and 367 clusters significantly increased iPSC generation (2-3× improvement). Addition of miR-302, -367, and -200c to Y4F synergistically increased iPSC generation.

Importantly, all microRNAs without Y4F did not generate any iPSC clone. When Y4F and all three microRNA clusters were combined, iPSC colonies were very close to authentic human iPSC colonies (FIG. 3). When Y4F and all three microRNA clusters were combined, there were much less numbers of non-iPSC and transformed colonies (FIG. 4,5). When Y4F and all three microRNA clusters were combined, iPSC colonies were formed much faster with more authentic morphology and gene expression (FIG. 5).

Taken together, our novel findings show that optimal combinations of transcription factors and microRNAs synergistically generate human iPSC colonies with much higher efficiency, with much higher speed, with much higher quality regardless of the vectors (viral or episomal). Thus, appropriate combination of transcription factors and microRNAs can be used for synergistically generating iPSC colonies (e.g., mRNAs encoding transcription factors and mature microRNAs or proteins of transcription factors and mature microRNAs, etc).

Example 8 microRNAs in Non-Integrative Vector: Episomal Vectors

Figure 6A:
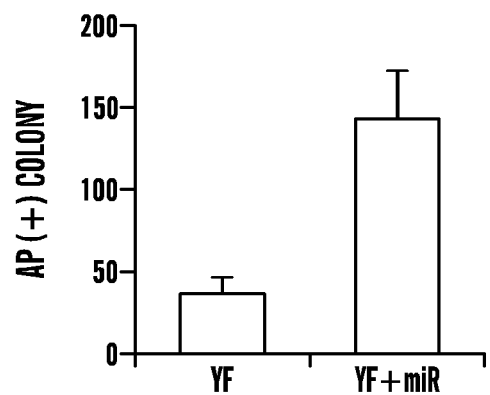
FIG. 6A-FIG. 6B shows experimental results that indicate episomal vector combinations providing synergistic effect in dedifferentiating cells. Addition of both miR-302 and 367 clusters significantly increased iPSC generation in both (A) human adult dermal fibroblasts and (B) human neonatal foreskin fibroblasts.
Figure 6B:
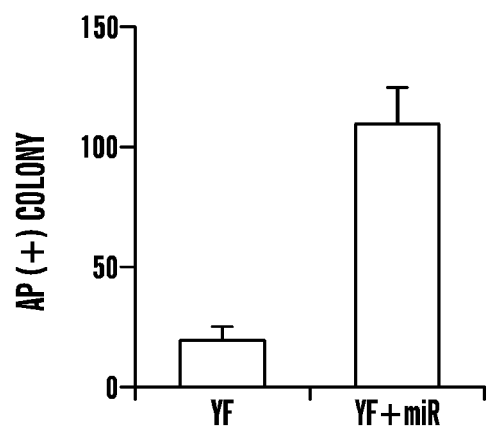

These combinations also similarly worked in non-viral episomal vectors. Using the Yamanaka four factors (Y4: Oct-4, Sox-2, Klf-4, and c-Myc (or 1-Myc) and microRNAs encoded in non-integrative episomal vectors, many iPSC-like colonies were generated. Similar to the results in lentivirus, addition of one of pluripotency-related microRNAs (miR-200c cluster) abolishes generation of iPSCs, and addition of both miR-302 and 367 clusters significantly increased iPSC generation in both human adult dermal fibroblasts (FIG. 6A) and human neonatal foreskin fibroblasts (FIG. 6B) (4-6 fold). Again, addition of miR-302, -367, and -200c to Y4F synergistically increased iPSC generation. Thereby demonstrating the robustness of the above described methods as agnostic to the platform for delivery. Importantly, successful application into non-integrative episomal vector virtually eliminates the risk of chromosomal integration/disruption.

Example 9 microRNAs in Non-Integrative Virus: Adenovirus

It is expected that essentially the same results will be generated from using an Adenovirus delivery system. Reprogramming transcription factors, Oct-4, Sox-2, Klf-4, and c-Myc and the aforementioned microRNAs can be encoded in Adenovirus, and successful generation of many iPSC-like colonies is expected. Similar to the results in lentivirus and episomal vectors, the miR-200c cluster is expected to abolish generation of iPSCs, and addition of both miR-302 and 367 clusters is expected to significantly increase iPSC generation (2-3× improvement). Again, addition of miR-302, -367, and -200c to Y4F is expected to provide a powerful synergistic increase in iPSC generation.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are sources of somatic and non-embryonic cells, methods of reprogramming somatic and non-embryonic cells, including use of reprogramming factors and microRNAs, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of generating mammalian patient-specific induced pluripotent stem cells for treating a patient, comprising:
   providing a quantity of mammalian somatic or non-embryonic cells from the patient;
   contacting the mammalian somatic or non-embryonic cells with a quantity of one or more reprogramming factors and one or more microRNA molecules; and
   culturing the somatic or non-embryonic cells for a period of time sufficient to generate at least one induced pluripotent stem cell,
   wherein the one or more microRNA molecules consist of (i) at least one miR-302 cluster member and (ii) at least one miR-200 cluster member, and
   wherein the quantity of reprogramming factors comprises at least Oct-4, Sox-2, Klf-4, and at least one of c-Myc or l-Myc.

2. The method of claim 1, wherein contacting the cells with a quantity of the one or more reprogramming factors and one or more microRNA molecules comprises transduction, nucleofection, electroporation, direct injection and/or transfection.

3. The method of claim 1, wherein the quantity of one or more reprogramming factors further comprise one or more factors selected from the group consisting of: Nanog, Sal14, Fbx-15, Utf-1, Tert, Lin-28, SV40 Large T Antigen ("SV40LT"), and short hairpin RNAs targeting p53 ("shRNA-p53").

4. The method of claim 1, wherein the at least one miR-200 cluster member comprises microRNAs selected from the group consisting of miR-200a, miR-200b, miR-200c, miR-141, miR-429, and derivatives and orthologs thereof.

5. The method of claim 1, wherein the at least one miR-302 cluster member comprises at least one microRNA selected from the group consisting of miR-302a, miR-302b, miR-302c, miR-302d, miR-367, and derivatives and orthologs thereof.

6. The method of claim 1, wherein the at least one miR-302 cluster member comprises at least one microRNA selected from the group consisting of miR-302a, miR-302b, miR-302c, miR-302d, and miR-367, and the at least one miR-200 cluster member comprises at least one microRNA selected from the group consisting of miR-200a, miR-200b, miR-200c, miR-141, and miR-429.

7. The method of claim 1, wherein the one or more microRNA molecules further comprise one or more microRNAs selected from the group consisting of miR-106a, miR-106b, miR-106b25, miR-20b, miR-93, miR-17, miR-291a, miR-291b-5p, miR-294, miR-295, miR-25, miR-32, miR92a-1, miR92a-2, miR92b, miR-363, miR-19a, miR-19b, miR-290-5p, miR-292, miR-20a, miR-290-3p, miR-18b, miR-291b-3p, miR-293, miR-369-5p, and derivatives and orthologs thereof.

8. The method of claim 1, wherein the quantity of one or more reprogramming factors and one or more microRNA molecules are encoded in one or more viruses or in one or more non-integrative vectors.

9. The method of claim 8, wherein the one or more viruses are non-integrative viruses.

10. The method of claim 9, wherein the non-integrative virus is an Adenovirus or Sendai virus.

11. The method of claim 1, wherein the one or more microRNA molecules are mature microRNA molecules.

12. The method of claim 8, wherein the non-integrative vector is an episomal or minicircle vector.

13. The method of claim 1, wherein the culturing is in a reprogramming media and the reprogramming media comprises at least one chemical induction molecule.

14. The method of claim 1, wherein the culturing is in a reprogramming media for at least 7 days.

15. The method of claim 13, wherein culturing the somatic or non-embryonic cells in a reprogramming media is for at least 7, 8, 9, 10, 11, 12, 13, 14, 15, or 16 days.

16. The method of claim 1, wherein generating induced pluripotent stem cells comprises further culturing the somatic or non-embryonic cells in an induction media is for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days.

17. The method of claim 16, wherein the induction media is serum-free media.

18. The method of claim 1, further comprising isolating at least one induced pluripotent stem cell.

19. The method of claim 11, wherein the mature microRNAs are selected from the group consisting of SEQ ID NO:10, SEQ ID NO:11, SEQ ID NO:12, SEQ ID NO:13, SEQ ID NO:20, and SEQ ID NO:25.

20. The method of claim 1, wherein the quantity of one or more reprogramming factors are proteins or mRNAs encoding the quantity of reprogramming factors.

21. A population of mammalian patient-specific induced pluripotent stem cells produced by the method of claim 1.

* * * * *

UNITED STATES PATENT AND TRADEMARK OFFICE
CERTIFICATE OF CORRECTION

| | | |
|---|---|---|
| PATENT NO. | : 11,898,169 B2 | Page 1 of 1 |
| APPLICATION NO. | : 17/239059 | |
| DATED | : February 13, 2024 | |
| INVENTOR(S) | : Kwang-Soo Kim and Young Cha | |

It is certified that error appears in the above-identified patent and that said Letters Patent is hereby corrected as shown below:

On the Title Page

Lines 3-4 under Abstract (57), delete "contacting the contacting the" and insert -- contacting the --

In the Claims

In Column 31, Line 59, Claim 3, delete "Sa114," and insert -- Sall4, --

Signed and Sealed this
Seventeenth Day of December, 2024

Derrick Brent
*Acting Director of the United States Patent and Trademark Office*

SEQUENCE LISTING

```
<160> NUMBER OF SEQ ID NOS: 31

<210> SEQ ID NO 1
<211> LENGTH: 23
<212> TYPE: RNA
<213> ORGANISM: Homo sapiens

<400> SEQUENCE: 1
caaagugcua acagugcagg uag                                              23

<210> SEQ ID NO 2
<211> LENGTH: 21
<212> TYPE: RNA
<213> ORGANISM: Homo sapiens

<400> SEQUENCE: 2
uaaagugcug acagugcaga u                                                21

<210> SEQ ID NO 3
<211> LENGTH: 23
<212> TYPE: RNA
<213> ORGANISM: Homo sapiens

<400> SEQUENCE: 3
caaagugcuc auagugcagg uag                                              23

<210> SEQ ID NO 4
<211> LENGTH: 23
<212> TYPE: RNA
<213> ORGANISM: Homo sapiens
```

```
<400> SEQUENCE: 4
caaagugcug uucgugcagg uag                                          23

<210> SEQ ID NO 5
<211> LENGTH: 23
<212> TYPE: RNA
<213> ORGANISM: Homo sapiens

<400> SEQUENCE: 5
caaagugcuu acagugcagg uag                                          23

<210> SEQ ID NO 6
<211> LENGTH: 22
<212> TYPE: RNA
<213> ORGANISM: Homo sapiens

<400> SEQUENCE: 6
caucaaagug gaggcccucu cu                                           22

<210> SEQ ID NO 7
<211> LENGTH: 22
<212> TYPE: RNA
<213> ORGANISM: Homo sapiens

<400> SEQUENCE: 7
gaucaaagug gaggcccucu cc                                           22

<210> SEQ ID NO 8
<211> LENGTH: 22
<212> TYPE: RNA
<213> ORGANISM: Homo sapiens

<400> SEQUENCE: 8
aaagugcuuc ccuuuugugu gu                                           22

<210> SEQ ID NO 9
<211> LENGTH: 23
<212> TYPE: RNA
<213> ORGANISM: Homo sapiens

<400> SEQUENCE: 9
aaagugcuac uacuuuugag ucu                                          23

<210> SEQ ID NO 10
<211> LENGTH: 23
<212> TYPE: RNA
<213> ORGANISM: Homo sapiens

<400> SEQUENCE: 10
uaagugcuuc cauguuuugg uga                                          23

<210> SEQ ID NO 11
<211> LENGTH: 23
<212> TYPE: RNA
<213> ORGANISM: Homo sapiens

<400> SEQUENCE: 11
uaagugcuuc cauguuuuag uag                                          23

<210> SEQ ID NO 12
<211> LENGTH: 23
<212> TYPE: RNA
<213> ORGANISM: Homo sapiens
```

```
<400> SEQUENCE: 12
uaagugcuuc cauguuucag ugg                                              23

<210> SEQ ID NO 13
<211> LENGTH: 23
<212> TYPE: RNA
<213> ORGANISM: Homo sapiens

<400> SEQUENCE: 13
uaagugcuuc cauguuugag ugu                                              23

<210> SEQ ID NO 14
<211> LENGTH: 22
<212> TYPE: RNA
<213> ORGANISM: Homo sapiens

<400> SEQUENCE: 14
cauugcacuu gucucggucu ga                                               22

<210> SEQ ID NO 15
<211> LENGTH: 22
<212> TYPE: RNA
<213> ORGANISM: Homo sapiens

<400> SEQUENCE: 15
uauugcacau uacuaaguug ca                                               22

<210> SEQ ID NO 16
<211> LENGTH: 21
<212> TYPE: RNA
<213> ORGANISM: Homo sapiens

<400> SEQUENCE: 16
uauugcacuu gucccggccu g                                                21

<210> SEQ ID NO 17
<211> LENGTH: 22
<212> TYPE: RNA
<213> ORGANISM: Homo sapiens

<400> SEQUENCE: 17
uauugcacuc gucccggccu cc                                               22

<210> SEQ ID NO 18
<211> LENGTH: 22
<212> TYPE: RNA
<213> ORGANISM: Homo sapiens

<400> SEQUENCE: 18
uauugcacuc gucccggccu cc                                               22

<210> SEQ ID NO 19
<211> LENGTH: 22
<212> TYPE: RNA
<213> ORGANISM: Homo sapiens

<400> SEQUENCE: 19
aauugcacgg uauccaucug ua                                               22

<210> SEQ ID NO 20
<211> LENGTH: 22
<212> TYPE: RNA
```

```
<213> ORGANISM: Homo sapiens

<400> SEQUENCE: 20
aauugcacuu uagcaauggu ga                                             22

<210> SEQ ID NO 21
<211> LENGTH: 23
<212> TYPE: RNA
<213> ORGANISM: Homo sapiens

<400> SEQUENCE: 21
ugugcaaauc uaugcaaaac uga                                            23

<210> SEQ ID NO 22
<211> LENGTH: 23
<212> TYPE: RNA
<213> ORGANISM: Homo sapiens

<400> SEQUENCE: 22
ugugcaaauc caugcaaaac uga                                            23

<210> SEQ ID NO 23
<211> LENGTH: 22
<212> TYPE: RNA
<213> ORGANISM: Homo sapiens

<400> SEQUENCE: 23
acucaaacua uggggggcacu uu                                            22

<210> SEQ ID NO 24
<211> LENGTH: 22
<212> TYPE: RNA
<213> ORGANISM: Homo sapiens

<400> SEQUENCE: 24
acucaaacug ggggcucuuu ug                                             22

<210> SEQ ID NO 25
<211> LENGTH: 23
<212> TYPE: RNA
<213> ORGANISM: Homo sapiens

<400> SEQUENCE: 25
uaauacugcc ggguaaugau gga                                            23

<210> SEQ ID NO 26
<211> LENGTH: 23
<212> TYPE: RNA
<213> ORGANISM: Homo sapiens

<400> SEQUENCE: 26
uaaagugcuu auagugcagg uag                                            23

<210> SEQ ID NO 27
<211> LENGTH: 23
<212> TYPE: RNA
<213> ORGANISM: Homo sapiens

<400> SEQUENCE: 27
aaagugccgc cuaguuuuaa gcc                                            23

<210> SEQ ID NO 28
<211> LENGTH: 23
```

```
<212> TYPE: RNA
<213> ORGANISM: Homo sapiens

<400> SEQUENCE: 28
uaaggugcau cuagugcugu uag                                             23

<210> SEQ ID NO 29
<211> LENGTH: 22
<212> TYPE: RNA
<213> ORGANISM: Homo sapiens

<400> SEQUENCE: 29
aaagugcauc cauuuuguuu gu                                              22

<210> SEQ ID NO 30
<211> LENGTH: 22
<212> TYPE: RNA
<213> ORGANISM: Homo sapiens

<400> SEQUENCE: 30
agugccgcag aguuuguagu gu                                              22

<210> SEQ ID NO 31
<211> LENGTH: 22
<212> TYPE: RNA
<213> ORGANISM: Homo sapiens

<400> SEQUENCE: 31
agaucgaccg uguuauauuc gc                                              22
```